United States Patent
Simonovic et al.

(10) Patent No.: US 10,672,156 B2
(45) Date of Patent: Jun. 2, 2020

(54) SYSTEMS AND METHODS FOR PROCESSING COMPUTATIONAL WORKFLOWS

(71) Applicant: Seven Bridges Genomics Inc., Cambridge, MA (US)

(72) Inventors: Janko Simonovic, Belgrade (RS); Sinisa Ivkovic, Belgrade (RS); Nebojsa Tijanic, Belgrade (RS)

(73) Assignee: SEVEN BRIDGES GENOMICS INC., Cambridge, MA (US)

( * ) Notice: Subject to any disclaimer, the term of this patent is extended or adjusted under 35 U.S.C. 154(b) by 0 days.

(21) Appl. No.: 15/454,811

(22) Filed: Mar. 9, 2017

(65) Prior Publication Data

US 2018/0053328 A1    Feb. 22, 2018

Related U.S. Application Data

(60) Provisional application No. 62/377,275, filed on Aug. 19, 2016.

(51) Int. Cl.
*G06T 11/20* (2006.01)

(52) U.S. Cl.
CPC .................. *G06T 11/206* (2013.01)

(58) Field of Classification Search
CPC ............... G06F 19/3418; G06T 11/206
See application file for complete search history.

(56) References Cited

U.S. PATENT DOCUMENTS

| | | |
|---|---|---|
| 7,100,147 B2 | 8/2006 | Miller et al. |
| 7,451,432 B2 | 11/2008 | Shukla et al. |
| 7,577,554 B2 | 8/2009 | Lystad et al. |
| 7,620,800 B2 | 11/2009 | Huppenthal et al. |
| 7,885,840 B2 | 2/2011 | Sadiq et al. |

(Continued)

FOREIGN PATENT DOCUMENTS

| | | |
|---|---|---|
| KR | 101282798 B1 | 7/2013 |
| WO | 2010010992 A1 | 1/2010 |

(Continued)

OTHER PUBLICATIONS

Kurs et al., Nextflow Workbench: Reproducible and Reusable Workflows for Beginners and Experts, bioRxiv, 2016.*

(Continued)

*Primary Examiner* — Michael Le
(74) *Attorney, Agent, or Firm* — Morgan, Lewis & Bockius LLP

(57) ABSTRACT

In one embodiment, a method of processing a computational workflow comprises receiving a description of a computational workflow. The description comprises a plurality of steps, in which each step has at least one input and at least one output, and further wherein an input from a second step depends on an output from a first step. The description is translated into a static workflow graph stored in a memory, the static workflow graph comprising a plurality of nodes having input ports and output ports, wherein dependencies between inputs and outputs are specified as edges between input ports and output ports. Information about a first set of nodes is then extracted from the static workflow graph and placed into a dynamic graph. A first actionable job is identified from the dynamic graph and executed.

20 Claims, 17 Drawing Sheets

(56) References Cited

U.S. PATENT DOCUMENTS

| | | | |
|---|---|---|---|
| 8,146,099 B2 | 3/2012 | Tkatch et al. | |
| 8,639,847 B2 | 1/2014 | Blaszczak et al. | |
| 9,184,988 B2 | 11/2015 | Bartlett et al. | |
| 9,250,886 B2 | 2/2016 | Gnech et al. | |
| 9,436,922 B2 | 9/2016 | Agarwal et al. | |
| 9,519,884 B2 | 12/2016 | Aron et al. | |
| 9,558,321 B2 | 1/2017 | Tijanic et al. | |
| 2002/0133504 A1 | 9/2002 | Vlahos et al. | |
| 2004/0078105 A1* | 4/2004 | Moon | G06Q 10/10 700/100 |
| 2004/0243982 A1 | 12/2004 | Robison | |
| 2005/0282137 A1 | 12/2005 | Sasinowski et al. | |
| 2010/0205588 A1* | 8/2010 | Yu | G06F 9/52 717/149 |
| 2012/0159491 A1* | 6/2012 | Aron | G06Q 10/06316 718/100 |
| 2013/0232480 A1 | 9/2013 | Winterfeldt et al. | |
| 2013/0311106 A1 | 11/2013 | White et al. | |
| 2013/0332081 A1 | 12/2013 | Reese et al. | |
| 2014/0095694 A1* | 4/2014 | Kimmet | G06F 11/3006 709/224 |
| 2014/0149725 A1 | 5/2014 | Gherman et al. | |
| 2014/0200147 A1 | 7/2014 | Bartha et al. | |
| 2014/0280360 A1 | 9/2014 | Webber et al. | |
| 2014/0281708 A1 | 9/2014 | Adam et al. | |
| 2015/0020061 A1 | 1/2015 | Ravi | |
| 2015/0066381 A1 | 3/2015 | Kural | |
| 2015/0066383 A1* | 3/2015 | Wernicke | G16B 50/00 702/20 |
| 2015/0161536 A1 | 6/2015 | Mikheev | |
| 2016/0011905 A1* | 1/2016 | Mishra | G06Q 10/06 718/102 |
| 2016/0103659 A1 | 4/2016 | Tijanic et al. | |
| 2016/0313874 A1 | 10/2016 | Mikheev | |
| 2017/0199764 A1 | 7/2017 | Tijanic et al. | |

FOREIGN PATENT DOCUMENTS

| | | |
|---|---|---|
| WO | 2013035904 A1 | 3/2013 |
| WO | 2016060910 A1 | 4/2016 |
| WO | 2016182578 A1 | 11/2016 |

OTHER PUBLICATIONS

Torri, 2012, Next generation sequence analysis and computational genomics using graphical pipeline workflows, Genes (Basel) 3(3):545-575.*

Kurs et al., Nextflow Workbench: Reproducible and Reusable Workflows for Beginners and Experts, bioRxiv, 2016 (Year: 2016).*

Torri, 2012, Next generation sequence analysis and computational genomics using graphical pipeline workflows, Genes (Basel) 3(3):545-575 (Year: 2012).*

Abouelhoda, 2012, Tavaxy: integrating Taverna and Galaxy workflows with cloud computing support, BMC Bioinformatics 13:77.

Agarwal, 2013, SINNET: Social Interaction Network Extractor from Text, Proc IJCNLP 33-36.

Alioto et al., A comprehensive assessment of somatic mutation detection in cancer using whole-genome sequencing, Nature Communications, Dec. 9, 2015.

Balhajjame et al., Using a suite of ontologies for preserving workflow-centric research objects, Web Semantics: Science, Services, and Agents on the World Wide Web, 2015, 16-42.

Cock, 2013, Galaxy tools and workflows for sequence analysis with applications in molecular plant pathology, Peer J 1:e167.

Cohen-Boulakia, 2014, Distilling structure in Taverna scientific workflows: a refactoring approach, BMC Bioinformatics 15(Suppl 1):S12.

Cromwell: A Workflow Management System geared towards scientific workflows. Available at: https://github.com/broadinstitute/cromwell/blob/29_hotfix/README.md. Accessed Sep. 26, 2017.

Deelman et al., Pegasus, a workflow management system for science automation, Future Generation Computer Systems, 2015, 17-35.

Dinov, 2011, Applications of the pipeline environment for visual informatics and genomic computations, BMC Bioinformatics 12:304.

Durham, 2005, EGene: a configurable pipeline system for automated sequence analysis, Bioinformatics 21 (12):2812-2813.

Gamma, Design Patterns: Elements of Reusable Object-Oriented Software with Applying Uml and Patterns: An Introduction to Object-Oriented Analysis and Design and the Unified Process (Chapter 3). Addison Wesley; 2003.

Goecks et al., Galaxy: a comprehensive approach for supporting accessible, reproducible, and transparent computational research in the life sciences, Genome Biology, 2010.

Guo, A workflow task scheduling algorithm based on the resources' fuzzy clustering in cloud computing environment, International Journal of Communication Systems (Abstract only), 2015, 28:1053-1067.

Hettne et al., Structuring research methods and data with the research object model: genomics workflows as a case study, Journal of Biomedical Semantics, 2014, 5:41.

Hoon, 2003, Biopipe: A flexible framework for protocol-based bioinformatics analysis, Genome Res 13(8):1904-1915.

Hull, 2006, Taverna: a tool for building and running workflows of services, Nucl Acids Res 34(Web Server issue): W729-32.

Kano, 2010, Text mining meets workflow: linking U-Compare with Taverna, Bioinformatics 26(19):2486-7.

Kanwal et al., Challenges of large-scale biomedical workflows on the cloud—a case study on the need for reproducibility of results, Computer-Based Medical Systems (CBMS), 2015 IEEE 28th International Symposium, 2015.

Kaushik et al., Rabix: an open-source workflow executor supporting recomputability and interoperability of workflow descriptions, Pac Symp Biocomput, 2016, 22:154-165.

Koster et al., Snakemake—a scalable bioinformatics workflow engine, Bioinformatics, 2012, vol. 28, No. 19, pp. 2520-1522.

Krabbenhoft, 2008, Integrating ARC grid middleware with Taverna workflows, Bioinformatics 24(9):1221-2.

Kuhn, 2010, CDK-Taverna: an open workflow environment for cheminformatics, BMC Bioinformatics 11:159.

Lanzen, 2008, The Taverna Interaction Service: enabling manual interaction in workflows, Bioinformatics 24 (8):1118-20.

Leipzig, A review of bioinformatic pipeline frameworks, Briefings in Bioinformatics, 2017, 18(3), 530-536.

Missier, 2010, Taverna, reloaded, Proc. Scientific and Statistical Database Management, 22nd Int Conf, Heidelberg, Germany, Jun./Jul. 2010, Gertz & Ludascher, Eds., Springer.

Nenadic, 2010, Nested Workflows, The Taverna Knowledge Blog, Dec. 13, 2010. Retrieved on Feb. 25, 2016 from http://taverna.knowledgeblog.org/2010/12/13/nested-workflows/.

O'Driscoll et al. 'Big Data,' Hadoop and cloud computing in genomics, 2013, pp. 774-781, vol. 46, Journal of Biomedical Informatics.

Oinn, 2004, Taverna: a tool for the composition and enactment of bioinformatics workflows, Bioinformatics 20 (17):3045-54.

Oinn, 2006, Taverna: lessons in creating a workflow environment for the life sciences, Concurrency and Computation: Practice and Experience 18(10):1067-1100.

Paterson, 2009, An XML transfer schema for exchange of genomic and genetic mapping data: implementation as a web service in a Taverna workflow, BMC Bioinformatics 10:252.

Peng, Reproducible Research in Computational Science, Science, Dec. 2, 2011, 334(6060), 1226-1227.

Potter, 2004, The ensemble analysis pipeline, Genome Res 14:934-941.

Sandve et al., Ten Simple Rules for Reproducible Computational Research, PLoS Computational Biology, Oct. 2013, vol. 9, Issue 10, e1003285.

Sroka, 2006, XQTav: an XQuery processor for Taverna environment, Bioinformatics 22(10):1280-1.

Sroka, 2010, A formal semantics for the Taverna 2 workflow model, J Comp Sys Sci 76(6):490-508.

(56) References Cited

OTHER PUBLICATIONS

Sroka, 2011, CalcTav—integration of a spreadsheet and Taverna workbench, Bioinformatics 27(18):2618-9.
Stallman, GNU Make: A Program for Directing Recompilation, Free Software Foundation, Inc., Jul. 2002.
Tan, 2010, A Comparison of Using Taverna and BPEL in Building Scientific Workflows: the case of caGrid, Concurr Comput 22(9):1098-1117.
Tan, 2010, CaGrid Workflow Toolkit: a Taverna based workflow tool for cancer grid, BMC Bioinformatics 11:542.
Terstyanszky et al., Enabling scientific workflow sharing through coarse-grained interoperability, Future Generation Computer Systems, 2014, 37, 46-59.
The Free Dictionary.com, Article about Client-server system originally from IGEL Technologies (2009) entitled: White Paper Cloud Computing: Thin clients in the cloud, Oct. 20, 2016 retrieval date; pp. 1-2.
The Free Dictionary.com, Article about Cloud computing originally from The Columbia Electronic Encyclopedia (2013) Oct. 20, 2016 retrieval date; Columbia Univ. Press—pp. 1-3.
Truszkowski, 2011, New developments on the cheminformatics open workflow environment CDK-Taverna, J Cheminform 3:54.
Turi, 2007, Taverna Workflows: Syntax and Semantics, IEEE Int Conf on e-Science and Grid Computing 441-448.
Vivian et al., Rapid and efficient analysis of 20,000 RNA-seq samples with Toil, bioRxiv, 2016.
Warneke et al., Nephele: Efficient Parallel Data Processing in the Cloud, ACM, 2009.
Wassink, 2009, Using R in Taverna: RShell v12. BMC Res Notes 2:138.
Wolstencroft, 2005, Panoply of Utilities in Taverna, Proc 2005 1st Int Conf e-Science and Grid Computing 156-162.
Wolstencroft, 2013, The Taverna Workflow Suite: Designing and Executing Workflows of Web Services on the Desktop, Web or in the Cloud, Nucl Acids Res 41(W1):W556-W561.
Yildiz, 2014, BIFI: a Taverna plugin for a simplified and user-friendly workflow platform, BMC Res Notes 7:740.
Yu, 2007, A tool for creating and parallelizing bioinformatics pipelines, DOD High Performance Computing Conf 417-420.
Zhang, 2013, Taverna Mobile: Taverna workflows on Android, EMBnet J 19(B):43-45.
Zhao, 2012, Why Workflows Break—Understanding and Combating Decay in Taverna Workflows, eScience 2012, Chicago, Oct. 2012.
Delcher, 1999, Alignment of whole genomes, Nucl. Acids Res 27(11):2369-76.
Dinov, 2014, The perfect neuroimaging-genetics-computation storm: collision of petabytes of data, millions of hardware devices and thousands of software tools, Brain Imaging and Behavior 8:311-322.
Dudley, 2009, A quick guide for developing effective bioinfornatics programming skills, PLoS Comput Biol 5(12): e1000589.
Fiers, 2008, High-throughput Bioinformatics with the Cyrilie2 Pipeline System, BMC Bioinformatics 9:96.
Hokamp, 2003, Wrapping up BLAST and Other Applications for Use on Unix Clusters, Bioinformatics 19(3)441-42.
International Search Report and Written Opinion dated Jan. 5, 2016, for International Patent Application PCT/US2015/054461 with International Filing Date Oct. 7, 2015, (7 pages).
Kawas, 2006, BioMoby extensions to the Taverna workflow management and enactment software, BMC Bioinformatics 7:523.
Li, 2008, Automated manipulation of systems biology models using libSBML within Taverna workflows, Bioinformatics 24(2):287-9.
Li, 2008, Performing statistical analyses on quantitative data in Taverna workflows: an example using R and maxdBrowse to identify differentially-expressed genes from microarray data, BMC Bioinformatics 9:334.
Li, 2010, A survey of sequence alignment algorithms for next-generation sequencing, Briefings in Bionformatics 11 (5):473-483.
Machine translation of KR 10-1282798 B1 generated on Jan. 6, 2016, by the website of the European Patent Office (23 pages).
Machine translation produced on Jun. 1, 2015, by Espacenet of WO 2010/010992 A1 (11 pages).
Machine translation produced on Jun. 1, 2015, by WPIO website of WO 2013/035904 (10 pages).
McKenna, 2010, The Genome Analysis Toolkit: a MapReduce framework for analyzing next-generation DNA sequencing data, Genome Res 20(9):1297-1303.
O'Rawe, 2013, Low Concordance of Multiple Variant-Calling Pipelines: Practical Implications for Exome and Genome Sequencing, Genome Med 5:28.
Pabinger, 2013, A survey of tools for variant analysis of next-generation genome sequencing data, Brief Bioinf.
Ramirez-Gonzalez, 2011, Gee Fu: a sequence version and web-services database tool for genomic assembly, genome feature and NGS data, Bioinformatics 27(19):2754-2755.
Rex, 2003, The LONI Pipeline Processing Environment, Neuroimage 19: 1033-1048.
Schenk, 2013, A pipeline for comprehensive and automated processing of electron diffraction data in IPLT, J Struct Biol 182(2):173-185.
Wen, 2012, Comparison of Open-Source Cloud Management Platforms: OpenStack and OpenNebula, 9th International Conference on Fuzzy Systems and Knowledge Discovery.

* cited by examiner

1020 →

1022

| VARIABLES | Value |
|---|---|
| W.I | input_file |
| W.O | |
| W.A.I | input_file |
| W.A.O | |
| W.B.I | |
| W.B.O | |

1024

| JOBS | #In | #Out |
|---|---|---|
| W | 0 | 1 |
| W.A | 0 | 1 |
| W.B | 1 | 1 |

1026

| LINKS | |
|---|---|
| W.I | W.A.I |
| W.A.O | W.B.I |
| W.B.O | W.O |

| VARIABLES | Value |
|---|---|
| W.I | input_file |
| W.O | |
| W.A.I | input_file |
| W.A.O | value_a |
| W.B.I | |
| W.B.O | |

1024

| JOBS | #In | #Out |
|---|---|---|
| W | 0 | 1 |
| W.A | 0 | 0 |
| W.B | 1 | 1 |

1026

| LINKS | |
|---|---|
| W.I | W.A.I |
| W.A.O | W.B.I |
| W.B.O | W.O |

| VARIABLES | Value |
|---|---|
| W.I | input_file |
| W.O | |
| W.A.I | input_file |
| W.A.O | value_a |
| W.B.I | value_a |
| W.B.O | |

1024

| JOBS | #In | #Out |
|---|---|---|
| W | 0 | 1 |
| W.A | 0 | 0 |
| W.B | 0 | 1 |

1026

| LINKS | |
|---|---|
| W.I | W.A.I |
| W.A.O | W.B.I |
| W.B.O | W.O |

| VARIABLES | Value |
|---|---|
| W.I | input_file |
| W.O | |
| W.A.I | input_file |
| W.A.O | value_a |
| W.B.I | value_a |
| W.B.O | value_b |

1024

| JOBS | #In | #Out |
|---|---|---|
| W | 0 | 1 |
| W.A | 0 | 0 |
| W.B | 0 | 0 |

1026

| LINKS | |
|---|---|
| W.I | W.A.I |
| W.A.O | W.B.I |
| W.B.O | W.O |

| VARIABLES | Value |
|---|---|
| W.I | input_file |
| W.O | value_b |
| W.A.I | input_file |
| W.A.O | value_a |
| W.B.I | value_a |
| W.B.O | value_b |

1024

| JOBS | #In | #Out |
|---|---|---|
| W | 0 | 0 |
| W.A | 0 | 0 |
| W.B | 0 | 0 |

1026

| LINKS | |
|---|---|
| W.I | W.A.I |
| W.A.O | W.B.I |
| W.B.O | W.O |

*FIG. 10I*

SYSTEMS AND METHODS FOR PROCESSING COMPUTATIONAL WORKFLOWS

CROSS-REFERENCE TO RELATED APPLICATIONS

This application claims priority from U.S. Provisional Patent Application Ser. No. 62/377,275, filed on Aug. 19, 2016, entitled Graph Theory Approaches for Optimizing Biomedical Data Analysis using Reproducible Workflows, the contents of which are hereby incorporated by reference.

BACKGROUND

The completion of the first human reference genome enabled the discovery of the whole catalogue of human genes, ushering in a new era of genomics research to discover the molecular basis of disease. More recently, so-called next generation sequencing (NGS) technologies can now routinely sequence entire genomes within days and for a low cost. The number of fully sequenced genomes continues to grow, and with it our understanding of human genetic variation. For example, the 1000 Genomes Project is an international collaboration that seeks to provide a comprehensive description of common human genetic variation by performing whole-genome sequencing of a diverse set of individuals from multiple populations. To that end, the 1000 Genomes Project has sequenced the genomes of over 2,500 unidentified people from about 25 populations around the world. See "A global reference for human genetic variation", *Nature* 526, 68-74 (2015). This has led to new insights regarding the history and demography of ancestral populations, the sharing of genetic variants among populations, and the role of genetic variation in disease. Further, the sheer number of genomes has greatly increased the resolution of genome wide association studies, which seek to link various genetic traits and diseases with specific genetic variants.

The path from sequencer output to scientifically and clinically significant information can be difficult even for a skilled geneticist or an academic researcher. Sequencer output is typically in the form of data files for individual sequence reads. Depending on the project goals, these reads may need to be quality checked, assembled, aligned, compared to the literature or to databases, segregated from one another by allele, evaluated for non-Mendelian heterozygosity, searched for known or novel variants, or subject to any of many other analyses. Such analytical processes are often modelled as computational workflows, in which the outputs of one step (e.g., software that performs quality checking) are provided as an input to another (e.g., software that performs sequence alignment).

Today, computational workflows are commonly used in many bioinformatics and genomics analyses. Computational workflows may consist of dozens of tools with hundreds of parameters to handle a variety of use cases and data types. Various computational workflow systems exist, including Taverna and the Graphical Pipeline for Computational Genomics (GPCG). See Wolstencroft et al., "The Taverna workflow suite: designing and executing workflows of Web Services on the desktop, web or in the cloud," Nucleic Acids Research, 41(W1): W557-W561 (2013); Torri et al., "Next generation sequence analysis and computational genomics using graphical pipeline workflows," Genes (Basel). 2012 Aug. 30; 3(3):545-75 (2012).

As the complexity of an individual workflow increases to handle a variety of use cases or criteria, it becomes more challenging to optimally compute with it. For example, analyses may incorporate nested workflows, business logic, memoization, parallelization, the ability to restart failed workflows, or require parsing of metadata—all of which compound the challenges in optimizing workflow execution. Further, increases in complexity make it challenging to port computational workflows to different environments or systems, which can lead to a lack of reproducibility. As a result of the increasing volume of biomedical data, analytical complexity, and the scale of collaborative initiatives focused on data analysis, reliable and reproducible analysis of biomedical data has become a significant concern. Accordingly, there is a need for improvements in computational workflow execution.

BRIEF SUMMARY

Large and increasing amounts of genomics data have resulted in a wide array of analysis methods and complexity. Reproducibility of results and portability across environments are key necessities for genomics studies, particularly as large, collaborative projects are becoming increasingly common. Workflow management systems help address these needs by providing a framework to reproducibly execute a sequence of analyses on large volumes of data across multiple environments. Optimizing workflow execution is thus critical for efficient, reliable analysis of genomics data.

Despite their utility, limitations exist in current state-of-the-art workflow platforms that impact their scalability, reproducibility, and efficiency. Existing workflow engines are often tied to a particular syntax. Such a restriction necessitates that all jobs in a workflow are described using the same workflow language, which limits scalability and is harmful to reproducibility. Additional data processing frameworks are limited in the efficiency of their execution. Conventional workflow engines require that in the case of parallelized or nested executables, the parent task must fully complete before downstream dependent tasks can begin. In the event that a downstream task's input is one of a plurality of outputs from the parent task, this delay in processing represents time that could have been spent executing later portions of the workflow. Embodiments of workflow engines of the present disclosure allow jobs to proceed based on the availability of intermediate results, thus decreasing processing time and cost. Additionally, in contrast to existing methods, embodiments of workflow engines of the present disclosure provide efficient execution without the need for extensive user annotation or specification of optimizations.

In one embodiment, a method of processing a computational workflow comprises receiving a description of a first computational workflow, the description comprising a plurality of steps, each step having at least one input and at least one output, wherein an input from a second step depends on an output from a first step. The description is then translated into a first graph stored in a memory, The first graph comprises a plurality of nodes having input ports and output ports, wherein dependencies between inputs and outputs are specified as edges between input ports and output ports. Translating can further comprise processing the description and creating a node in the first graph for each step in the plurality of steps, wherein steps that specify executable tools are marked as executable nodes and steps that specify containers are marked as container nodes. Once the first graph is created from the workflow description, information about a first set of nodes is extracted and placed into a second graph. The extracted information can comprise information related to jobs (e.g., actions that may be taken according to nodes), variables (e.g., values associated with input ports and output ports), and links (e.g., edges connecting input ports and output ports and defining the flow of data elements) defined by the first set of nodes. A first actionable job (e.g., a job for which values for its input ports have been supplied) is then identified or selected from the second graph and executed.

In some embodiments, the first graph is a static graph that is fully enumerated from the workflow description prior to placing information about its nodes into the second graph. This can comprise adding every step specified by the description to the static graph. In some embodiments, the second graph is a dynamic graph that uses the first graph as a reference to guide workflow execution.

In some embodiments, the first step references a description of a second computational workflow. In some of these embodiments, the description of the second computational workflow is written in a different format than the description of the first computational workflow. In further embodiments, translating the description of the first computational workflow comprises adding the first step as a container node to the first graph, accessing the description of the second computational workflow, and adding any steps described by the second computational workflow into the first graph. In further embodiments, the first set of nodes extracted from the first graph does not include nodes corresponding to steps described by the description of the second computational workflow. In these embodiments, the first set of nodes extracted from the first graph may not include nodes corresponding to steps described by the description of the second computational workflow. In some embodiments, the first actionable job comprises the first step, and executing the first actionable job comprises extracting, from the first graph, information about a second set of nodes. The second set of nodes comprises steps from the description of the second computational workflow. Information about the second set of nodes is then placed into the second graph. A second actionable job is then identified from the second graph. In further embodiments, the second actionable job comprises an executable component.

In some embodiments, the first actionable job represents an executable described by the first step, and executing the first actionable job comprises submitting the first actionable job to a backend executor. In these embodiments, the backend executor can be located on a device separate from the workflow execution engine. In further embodiments, the method can further comprise receiving, from the backend executor, an indication that the first actionable job has completed. The second graph is then updated with information related to an output generated by the completed first actionable job. A second actionable job is then identified from the second graph and executed. In further embodiments, updating the second graph can comprise updating a value for a variable, decrementing a port counter for a job related to an updated value, and determining whether any additional variables may be updated by considering links associated with the updated variable. In further embodiments, a value may then be updated for a determined additional variable.

In some embodiments, the inputs for the first actionable job comprise an array of values, and executing the first actionable job comprises placing a plurality of jobs in the second graph for the first actionable job. Each of the placed jobs can comprise the executable from the first actionable job and one value of the array of values. In these embodiments, the description of the first computational workflow can indicate that the step associated with the first actionable job can be scattered.

In another embodiment, a system for processing a computational workflow comprises at least one computer hardware processor and at least one non-transitory computer-readable storage medium storing processor-executable instructions. The instructions, when executed by the at least one computer hardware processor, cause the at least one computer hardware processor to receive a description of a first computational workflow, the description comprising a plurality of steps, each step having at least one input and at least one output, wherein an input from a second step depends on an output from a first step. The description of the computational workflow is then translated into a static workflow graph stored in a memory, the static workflow graph comprising a plurality of nodes having input ports and output ports, wherein dependencies between inputs and outputs are specified as edges between input ports and output ports. Translating can further comprising processing the description and creating a node in the static workflow graph for each step in the plurality of steps, wherein steps that specify executable tools are marked as executable nodes and steps that specify containers are marked as container nodes. Information about a first set of nodes is then extracted from the static workflow graph and placed into a control structure. The information can comprise information related to variables, jobs, and links defined by the first set of nodes. A first actionable job is then identified from the control structure. The first actionable job can comprise a job for which all of its inputs are available. The first actionable job is then executed.

In some embodiments, the first actionable job can comprise a container. In some embodiments, identifying a first actionable job from the control structure can comprise finding jobs having input counters set to zero. In further embodiments, the instructions can further comprise receiving an indication that the first job has completed, updating variables, jobs, and links the control structure based on the received indication, and identifying a second actionable job from the control structure, wherein the input for the second actionable job depends from the output of the first actionable job. In another embodiment, translating the description of the first computational workflow further comprises adding every step specified by the description to the workflow graph.

BRIEF DESCRIPTION OF THE DRAWINGS

FIGS. 1 through 13, wherein like parts are designated by like reference numerals throughout, illustrate an example embodiment of a system and method for the implementation of a sequence variation graph alignment system. Although the present disclosure describes the system and method with reference to the example embodiments described in the figures, it should be understood that many alternative forms can embody the present disclosure. One of ordinary skill in the art will additionally appreciate different ways to alter the parameters of the embodiments disclosed in a manner still in keeping with the spirit and scope of the present disclosure.

FIG. 1 is a block diagram illustrating an embodiment of a workflow execution system according to the disclosure;

FIG. 2 depicts an exemplary workflow description and workflow graph according to an embodiment of the disclosure;

FIG. 3 is a block diagram illustrating the workflow execution engine of FIG. 1 in further detail;

FIG. 4 is a block diagram illustrating another embodiment of a workflow execution system according to the disclosure;

FIG. 5 is a flow diagram illustrating an embodiment of a method processing a computational workflow according to an embodiment of the disclosure;

FIGS. 10A-I depict an example of processing a workflow description using methods according to the disclosure;

FIG. 11 depicts an embodiment of a static graph and two stages of a corresponding dynamic graph as a workflow is executed; and FIG. 12 is a flow diagram illustrating a method of scattering an actionable job according to the disclosure.

DETAILED DESCRIPTION

Figure 1:
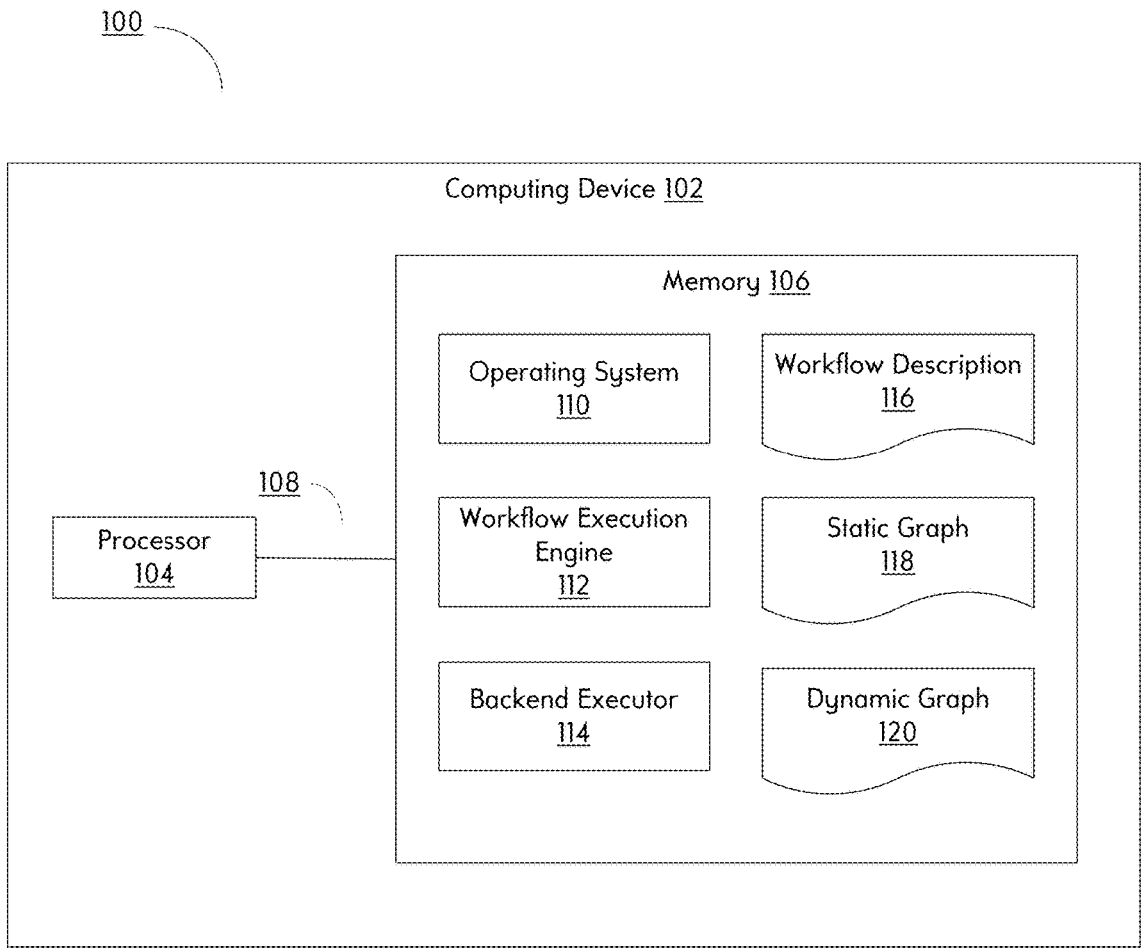

Workflow descriptions and the engines that interpret and execute them must be able to support a plethora of computational environments and ensure reproducibility and efficiency while operating across them. In recent years, the concept of organizing data analysis via computational workflows and accompanying workflow description languages has surged in popularity as a way to support the reproducible analysis of massive genomics datasets. However, the inventors have recognized and appreciated that large and complicated computational workflows are often specific for single architectures, preventing their reproducibility on other platforms. Further, a complex ecosystem of workflow languages has developed, preventing interoperability. Moreover, as the complexity of computational workflows increases, it becomes more challenging to optimally compute.

Robust and reliable workflow systems share three key properties: flexibility, portability, and reproducibility. Flexibility can refer to the ability to gracefully handle large volumes of data with multiple formats. Adopting flexibility as a design principle for workflows ensures that multiple versions of a workflow are not required for different datasets and a single workflow or pipeline can be applied in many use cases. Together, these properties reduce the software engineering burden accompanying large scale data analysis. Portability, or the ability to execute analyses in multiple environments, grants researchers the ability to access additional computational resources with which to analyze their data. For example, workflows highly customized for a particular infrastructure make it challenging to port analyses to other environments and thus scale or collaborate with other researchers. Well-designed workflow systems must also support reproducibility in science. In the context of workflow execution, computational reproducibility can be simply defined as the ability to achieve the same results on the same data regardless of the computing environment or when the analysis is performed. Workflows and the languages that describe them must account for the complexity of the information being generated from biological samples and the variation in the computational space in which they are employed. Without flexible, portable, and reproducible workflows, the ability for massive and collaborative genomics projects to arrive at synonymous or agreeable results is limited.

Accordingly, embodiments of the disclosure describe novel systems and methods for processing computational workflows that allow for a variety of workflow formats to execute in diverse environments, with reproducible results. Further, the techniques developed by the inventors significantly increase workflow efficiency and speed. In some embodiments, a workflow description is transformed into a workflow graph, resulting in a common format that can be generated from a variety of workflow languages. In further embodiments, execution of the workflow graph is transformed during runtime, providing for the ability to perform dynamic expressions, parallelize operations, and nest workflows within workflows, allowing for rapid decomposition (i.e., the identification of jobs) of complex workflows and the ability to quickly reuse existing code.

Some embodiments described herein address all of the above-described issues that the inventors have recognized with conventional techniques for processing computational or bioinformatics workflows. However, not every embodiment described herein addresses every one of these issues, and some embodiments may not address any of them. As such, it should be appreciated that embodiments of the technology described herein are not limited to addressing all or any of the above-described issues of conventional techniques for processing computational workflows.

Further, the detailed description set forth below in connection with the appended drawings is intended as a description of embodiments and does not represent the only forms which may be constructed and/or utilized. However, it is to be understood that the same or equivalent functions and sequences may be accomplished by different embodiments that are also intended to be encompassed within the spirt and scope of the disclosure.

Exemplary Workflow Execution System

FIG. 1 is a block diagram illustrating an embodiment of a workflow execution system 100 suitable for practicing exemplary embodiments of the present disclosure. The workflow execution system 100 may be used for processing a description of a computational workflow, such as a Common Workflow Language (CWL) workflow. In this embodiment, the workflow execution system 100 comprises a computing device 102, which may include a processor 104 in communication with a memory 106 over a bus 108. The memory 106 may include instructions or codes that when executed by the processor 104 implement an operating system 110, a workflow execution engine 112, and a backend executor 114. The memory 106 may further store a workflow description 116, which can describe a computational workflow, and a first graph, such as a static graph 118. The static graph 118 is a representation of the workflow description 116 as a directed acyclic graph (DAG), in which applications or components of the workflow become nodes and edges indicate the flow of data elements between ports of linked tools. The workflow execution engine 112 may create the static graph 118 from the workflow description 116, and further populate a second graph, such as a dynamic graph 120, with information from the static graph 118. The dynamic graph 120 may be used as a control structure by the workflow execution engine 112 to process and execute the workflow description 116, allowing for transformations and optimizations during runtime. Jobs identified as actionable from the dynamic graph may be supplied to the backend executor 114 (which may also be termed a "backend"), which executes an actionable job and communicates with the workflow execution engine 112 when the job is complete.

Depending on particular implementation requirements of the present disclosure, the computing device 102 may be any type of computing system, such as a workstation, server, desktop computer, laptop, handheld computer, mobile device, cloud computing instance, or any other form of computing device or system. Further, the computing device 102 may have sufficient processing power and memory capacity to perform all or part of the operations described herein. Alternately, all or parts of the computing device 102 may be embodied as a stand-alone system, or as a component of a larger electronic system within any kind of environment. In certain embodiments, the workflow execution system 100 may comprise multiples of computing devices 102, which may be differently configured.

The processor 104 may include hardware or software-based logic to execute instructions on behalf of the computing device 102. For example, depending on specific implementation requirements, the processor 104 may include a microprocessor; single or multiple cores for executing software stored in the memory 106; an application-specific integrated circuit (ASIC); a graphics processing unit (GPU); a distributed processor, such as a cluster or network of processors or computing systems; a virtual or logical processor of a virtual machine; or other hardware or software components for controlling the computing device 102.

The memory 106 is a processor-readable medium that stores instructions, codes, data, or other information. As used herein, a processor-readable medium is any medium that stores instructions, codes, data, or other information non-transitorily and is directly or indirectly accessible to a processor. For example, the memory 106 can be a volatile random access memory (RAM), a persistent data store such as a hard-disk drive or a solid-state drive, a compact disc (CD), a digital versatile disc (DVD), a Secure Digital™ (SD) card, a virtual or networked drive, or any combination thereof. In some embodiments, the memory 106 can be integrated with the processor(s) 104, separate from the processor 104, or external to the workflow execution system 100.

Various applications, such as the workflow execution engine 112 and backend executor 114, may run on the operating system 110. The operating system 110 may comprise any of the versions of the conventional operating systems, any embedded operating system, any real-time operating system, any open source operating system, any proprietary operating system, or any other operating system capable of running on the computing device 102 and performing all or part of the operations described herein. Further, the operating system 110, workflow execution engine 112, and backend executor 114 may in some instances be accessed or run from a bootable CD, thumb drive, or from a network.

The workflow description 116 can describe a computational or bioinformatics workflow. As previously noted, computational workflows can comprise dozens of tools with hundreds of parameters to handle a variety of use cases and data types. In practice, workflows are described with machine-readable serialized data objects in either a general-purpose programming language, domain-specific language, or serialized object models for workflow description. For example, an object model-based approach may describe the steps in a workflow in JavaScript Object Notation (JSON) format with a custom syntax. Similarly, the workflow description can be written using Common Workflow Language (CWL). CWL is a specification that allows one to describe various command line tools and to connect them together to create workflows. CWL is similar to tools such as GNU "make" as it specifies an order of execution based on dependencies between tasks. However, CWL further requires that tasks be isolated and have explicit values for both inputs and outputs. More information regarding CWL can be found at http://www.commonwl.org. Additionally, it should be noted that embodiments of the disclosure may use a variety of formats of workflow descriptions, including Workflow Description Language (WDL), eXtensible Markup Language (XML), and the like.

A workflow description typically describes a series of interconnected "steps", each of which can be a single tool or another, previously-described, workflow. Each step in the workflow has a set of "ports" which represent data elements that are either inputs or outputs of the associated tool or workflow. A single port represents a specific data element that is required for execution of the tool, or is a product of the execution of the tool. For data elements which are passed between applications, there must be an output port from the upstream tool and a complementary input port on the downstream application. Data elements received as inputs are typically processed by the underlying tool or workflow associated with a step, transforming the data into an output that may be supplied to subsequent steps.

Figure 2:
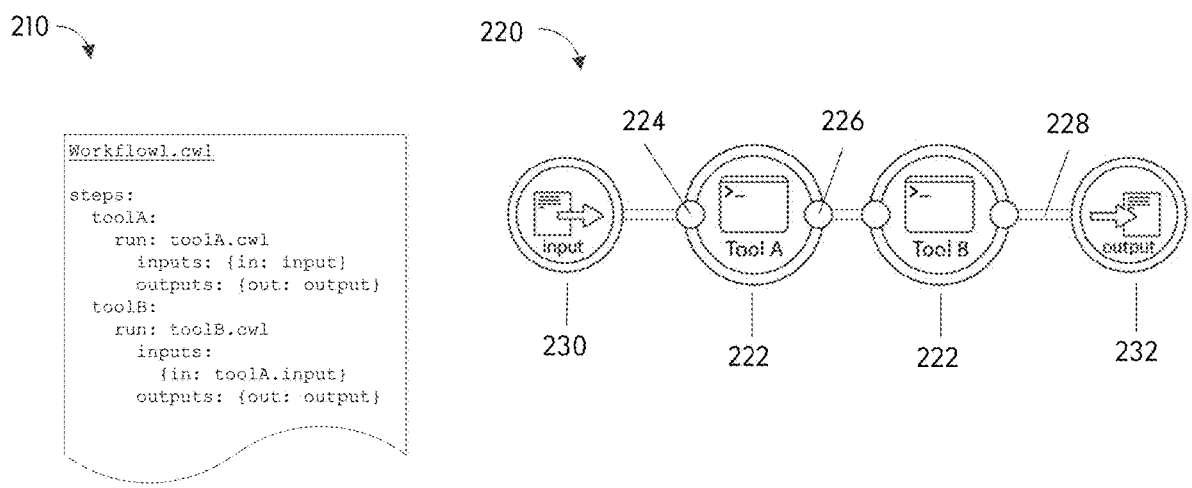

The static graph 118 is a representation of the workflow description 116 as a directed acyclic graph (DAG). When a workflow description is represented as a DAG, applications become nodes and edges indicate the flow of data elements between ports of linked tools. Similarly, as steps of a workflow can describe additional embedded workflows or elements, nodes can also represent "containers" storing embedded portions of the graph. Such nodes may be termed container nodes. FIG. 2 illustrates an example of a workflow description 210 and a corresponding static graph 220. As shown in FIG. 2, the workflow description 210 includes two steps that describe executing the output from a tool A using a tool B. A representation of the workflow description 210 as a static graph 220 includes two nodes 222 representing the tools A and B. The nodes 222 have input ports 224 and output ports 226, which define discrete data elements, such as an input file 230, that are passed downstream along a set of edges 228 to generate a processed output 232.

Of course, workflow descriptions and corresponding static graphs can be more complicated. For example, a workflow describing a whole genome analysis to study the complete DNA sequence of an organism may contain dozens of interconnected tools providing various functionality related to quality control, file transformations, alignment, variant calling, and the like. Each of these tools may include specific optimizations, including the type of computational instance best suited for running a tool (e.g., due to memory or processing requirements). In some cases, the workflow itself may include specific optimizations in order to obtain optimal usage of instance resources and avoid creating unnecessary processes. For example, the workflow may segment an alignment into several regions of the genome, which can be processed in parallel on separate instances. One specific example of such a workflow is the Seven Bridges® "Whole Genome Analysis—BWA+GATK 2.3.9-Lite (with Metrics)" workflow, available in CWL format at https://igor.sbgenomics.com/public/apps.

It should be noted that in this embodiment, the static graph 118 is static in the sense that once it has been generated and includes information from the workflow description 116, it is not modified during subsequent execution or processing of the workflow. Rather, the static graph 118 is used as a reference to guide construction of the dynamic graph 120. In this way, the workflow execution engine 112 has full visibility of the entire workflow via the static graph 118, but can efficiently apply optimizations by generating and modifying the dynamic graph 120 during execution.

In practice, the static graph 118 may be represented and stored in a computer memory, such as the computer memory 106 of FIG. 1. For example, a node can be a portion of the memory 106, which can include entries within a database, files or portions of one or more files within a file system, a set of tables describing nodes, edges, and other properties of the graph, and the like. More specifically, a node can be one or more memory locations at which properties or characteristics of that node (e.g., fields associated with the associated step in the workflow description 116, such as the tool to be run, associated parameters and flags) and references or relationships between that node and other nodes (e.g., the flow of data elements between steps) are stored. These relationships and references between nodes can be referred to as the edges of the graph. As a specific example, a node can be a portion of a memory at which a list of edges of that node (or edges adjacent to or incident upon that node) are stored.

The workflow execution engine 112 may comprise a library of logical and statistical code that, when loaded into memory 106 and executed by processor 104, processes the workflow description 116 by identifying actionable jobs and submitting them for execution. The workflow execution engine 112 can identify actionable jobs by interacting with the dynamic graph 120, which is used by the workflow execution engine 112 to monitor, automate, and optimize workflow execution. The dynamic graph 120 is initially populated with information from the static graph 118, which acts as a reference. Further, transformations may be applied to the dynamic graph 120 in order to optimize workflow execution. Once actionable jobs are identified, they may be submitted to the backend executor 114 for execution.

In some embodiments, the workflow execution engine 112 can register one or more backend executors 114 to execute actionable jobs. For example, the workflow execution engine 112 may identify an actionable job that comprises an executable, one or more input files, and other parameters specified by the workflow description 116. The actionable job may then be submitted to the backend executor 114. To process the job, the backend executor may retrieve the executable (e.g., as a Docker container), identify related parameters, and access any needed files or data. The files may be stored on a network and accessed via a network filesystem, or alternately may be directly uploaded or copied to the memory 106. When a job completes, the backend executor 114 may send a signal or event to the workflow execution engine 112 indicating that the job has completed. Such an event can further include instructions to retrieve any outputs or data files generated by the completed job.

Figure 3:
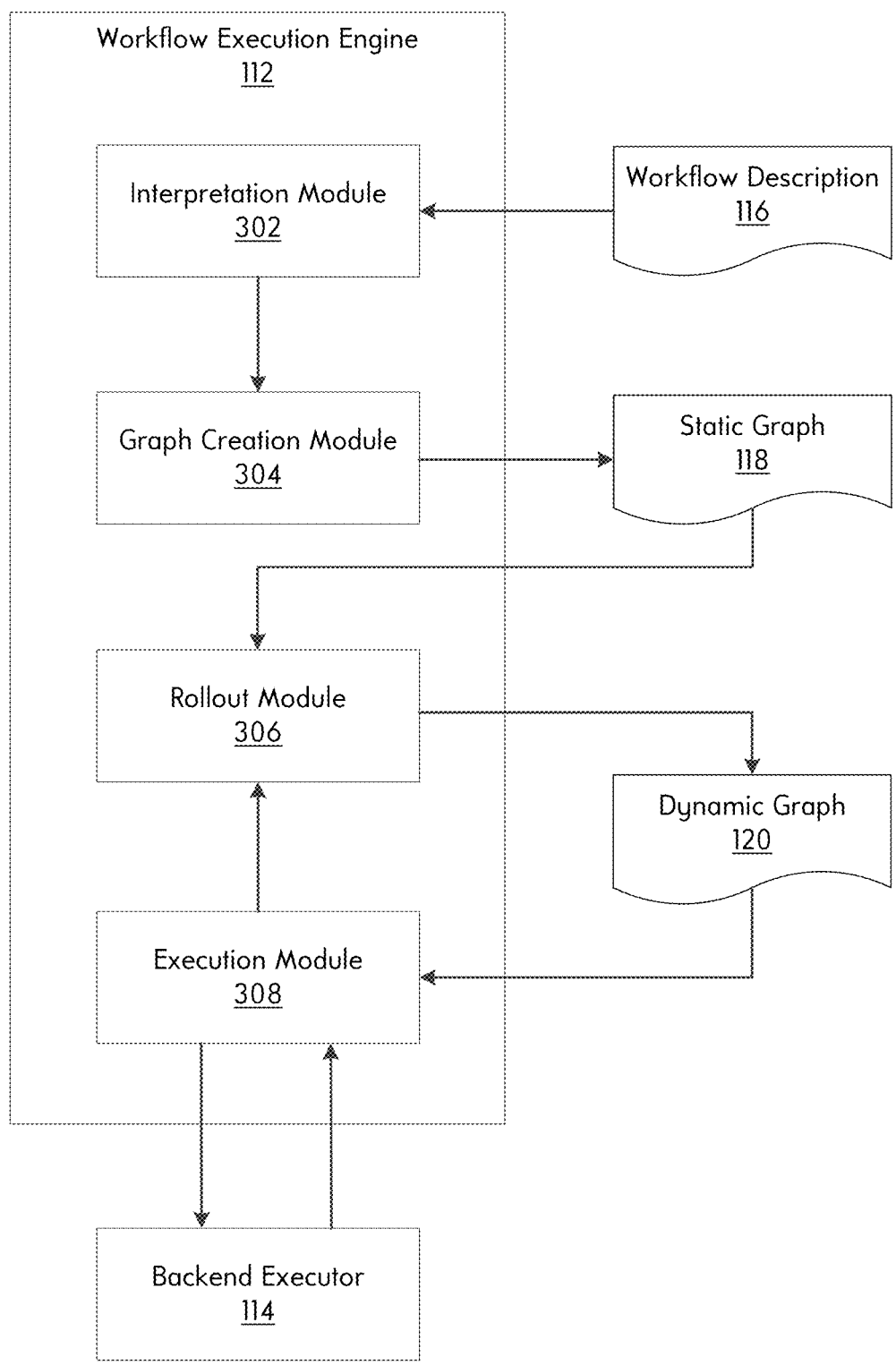

FIG. 3 illustrates the workflow execution engine 112 of FIG. 1 in further detail. As shown in FIG. 3, the workflow execution engine 112 can further comprise a workflow interpretation module 302, a graph creation module 304, a rollout module 306, and an execution module 308. Each of the modules 302, 304, 306, 308 describe programs or software that implement various functions that may be associated with a graph alignment system according to the disclosure. The terms "program" or "software" are used herein in a generic sense to refer to any type of computer code or set of processor-executable instructions that can be employed to program a computer or other processor to implement various aspects of embodiments as discussed herein. Additionally, it should be appreciated that according to one aspect, one or more computer programs that when executed perform methods of the disclosure provided herein need not reside on a single computer or processor, but may be distributed in a modular fashion among different computers or processors to implement various aspects of the disclosure provided herein. Accordingly, while the present disclosure is illustrated with reference to the modules 302, 304, 306, 308, as will be appreciated by those of skill in the art, other configurations and/or combinations fall within the scope of the disclosure.

Data structures may be stored in one or more non-transitory computer-readable storage media in any suitable form. For simplicity of illustration, data structures may be shown to have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

Also, various inventive concepts may be embodied as one or more processes, of which examples have been provided. The acts performed as part of each process may be ordered in any suitable way. Accordingly, embodiments may be constructed in which acts are performed in an order different than illustrated, which may include performing some acts simultaneously, even though shown as sequential acts in illustrative embodiments.

Processor-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

The workflow interpretation module 302 is configured to interpret an incoming workflow description, such as the workflow description 116 of FIG. 1. As previously noted, workflows may be described using a variety of formats, such as XML, CWL, WDL, and the like. The workflow interpretation module 302 may be configured to understand and interpret one or more formats, e.g., via the use of separate bindings specific for each format. The ability for the workflow execution engine 112 to interpret multiple workflow formats is advantageous at least because it allows for mixed protocols. For example, a workflow description may reference one or more other workflow descriptions, e.g. by reciting a container node of which contents may be found a second workflow description file. In some cases, the second workflow description file may be in a different format from the first. The ability to process multiple workflow description formats is particularly useful in the fields of bioinformatics and genomics due to the wide variety of formats in use. Thus, some embodiments of the disclosure can translate various workflow descriptions, regardless of format, into a common format, such as the static graph 118, which may then be processed to effect all of the components of the workflow. In practice, the interpretation module 302 can comprise a set of bindings written to independently process each workflow description format.

Once the workflow description 116 has been interpreted, the graph creation module 304 creates a static graph, such as the static graph 118 of FIG. 1. Once generated, the static graph 118 includes every operation or step described in the workflow description 116, and thus describes a minimal set of operations required to process the workflow. It may be possible to perform transformations of the workflow in order to allow for additional opportunities for computational optimization. Modern workflow description languages often allow for external transformations of the data elements in the workflow graph to enable more flexibility in the workflow description. Due to these external transformations, additional edges and nodes could be created in a workflow graph during execution, which in turn could be decomposed into additional jobs for optimization. However, it is difficult to do this generally. If an engine is capable of performing decompositions of jobs even when the workflow has external transformations, further optimizations can be made to reduce cost or time of an analysis.

In some embodiments, the use of a second graph to decompose a workflow into a plurality of jobs allows for various optimizations, including the ability to efficiently process embedded workflows and to parallelize or "scatter" portions of the workflow. Accordingly, in some embodiments, the static graph 118, once generated by the graph creation module 304, is a static structure that remains unchanged throughout the execution of the workflow. Instead, transformations are performed using a separate structure, such as the dynamic graph 120. The dynamic graph 120 may be used to automate and monitor execution, while simultaneously allowing for the transformation of graph elements by generalizing nodes of the static graph 118 to include transformations, such as when parallelization is possible at a given node. Accordingly, the workflow execution engine 112 may interact with the dynamic graph 120 to optimize execution of the workflow at runtime, allowing for fine decompositions of jobs specified by the static graph 118.

The use of two graphs, i.e., a static graph and a dynamic graph, is a useful feature that can improve flexibility and optimize execution. In particular, translating a workflow description into a static graph allows for the abstraction of various workflow formats into a single common format. The common format may then be processed by a workflow execution engine to execute the workflow. Second, selectively populating a dynamic graph with information from the static graph allows for additional transformations of nodes during runtime. For example, portions of a workflow may take longer to execute depending on hardware used by backend executors. In such cases, an optimal execution strategy cannot be determined until runtime. Thus, during runtime, the dynamic graph can flexibly accommodate the variable completion of jobs, transforming the dynamic graph and looking ahead to downstream jobs only when needed.

As shown in FIG. 3, the rollout module 306 populates the dynamic graph 120 with, e.g., information from the static graph 118. This can include information about variables, jobs, and links specified by the static graph 118. In particular, variables can include ports and their explicit values, if available; jobs can include information about each node of the static graph 118, and a counter for the inputs and outputs that have been evaluated at that node; and links can include the edges in the workflow graph connecting particular inputs and outputs. The dynamic graph 120 can be similarly stored in a memory as the static graph 118. For example, the dynamic graph 120 can be a list of nodes and edges. In some embodiments, the dynamic graph 120 can be a set of tables storing information about variables, jobs, and links.

In some embodiments, the rollout module 306 may populate the dynamic graph 120 with only a subset of the information from the static graph 118. For example, the rollout module 306 may populate the dynamic graph with information from only first-level nodes in the graph. First-level nodes can include container nodes and nodes, but not the contents of the container nodes (which may be deemed to be another level away, and embedded by that node). As the execution engine 112 executes the workflow, it may encounter a container node in the dynamic graph 120. When container nodes are encountered, the execution engine 112 may direct the rollout module 306 to evaluate those container nodes within the static graph 118 and to subsequently add their contents (e.g., additional nodes or container nodes specified by that container node) to the dynamic graph 120.

Further, in some embodiments, nodes representing executable tools may be subsequently marked as container nodes in the dynamic graph 120, allowing for further transformations of the dynamic graph 120. For example, if a node has a port that is scatterable, the node may be replaced by a container node (or "scatter wrapper") and the rollout module 306 can perform further optimizations of that node as will be described in further detail below.

The execution module 308 coordinates the processing of the workflow. For example, the execution module 308 can select actionable jobs from the dynamic graph 120. Certain actionable jobs can represent applications (e.g., a command line tool), which can be submitted for execution to the backend executor 114. When a job completes, the execution module 308 can receive a corresponding event from the backend executor 114. The event may cause the execution module 308 to update the dynamic graph 120 with new information generated by the event, such as the value of a variable associated with a completed output port. In turn, this may cause the execution module 308 to consider whether the values of any additional variables may be updated by considering whether there are any associated links (i.e., edges) connecting other input ports or output ports with the completed output port. This may result in new jobs becoming actionable, as the inputs or outputs they depend from become available.

Other actionable jobs may represent containers. When the execution module 308 encounters an actionable job that is a container, it can coordinate with the rollout module 306 in order to add information about those containers to the dynamic graph 120. For example, a container may represent a nested workflow. In this case, the rollout module 306 would then add all first-level nodes within that container into the dynamic graph 120. Once the rollout is complete, the execution module 308 may then identify whether there are any new actionable jobs as a result of the rollout. This can comprise considering whether the values of any additional variables may be updated according to links (i.e., input ports and output ports that are connected by edges) added as a result of the rollout, which can result in new jobs becoming actionable.

In some embodiments, the execution module 308 can mark certain actionable jobs that represent applications as container nodes. For example, CWL allows for the parallelization of nodes via a technique known as "scatter/gather." When a workflow description describes a port as "scatterable," the associated step can be parallelized over a list of input elements provided to that port. For example, a step that includes aligning a plurality of sequence reads against the human genome could be scattered against each chromosome. When the execution module 308 encounters a port that is scatterable, it can transform that node by instructing the rollout module to create a plurality of jobs for that node within the dynamic graph 120 instead of a single job. In this way, the execution module 308 can use the static graph 118 as a scaffold to guide execution, while introducing additional optimizations via the dynamic graph 120.

Figure 4:
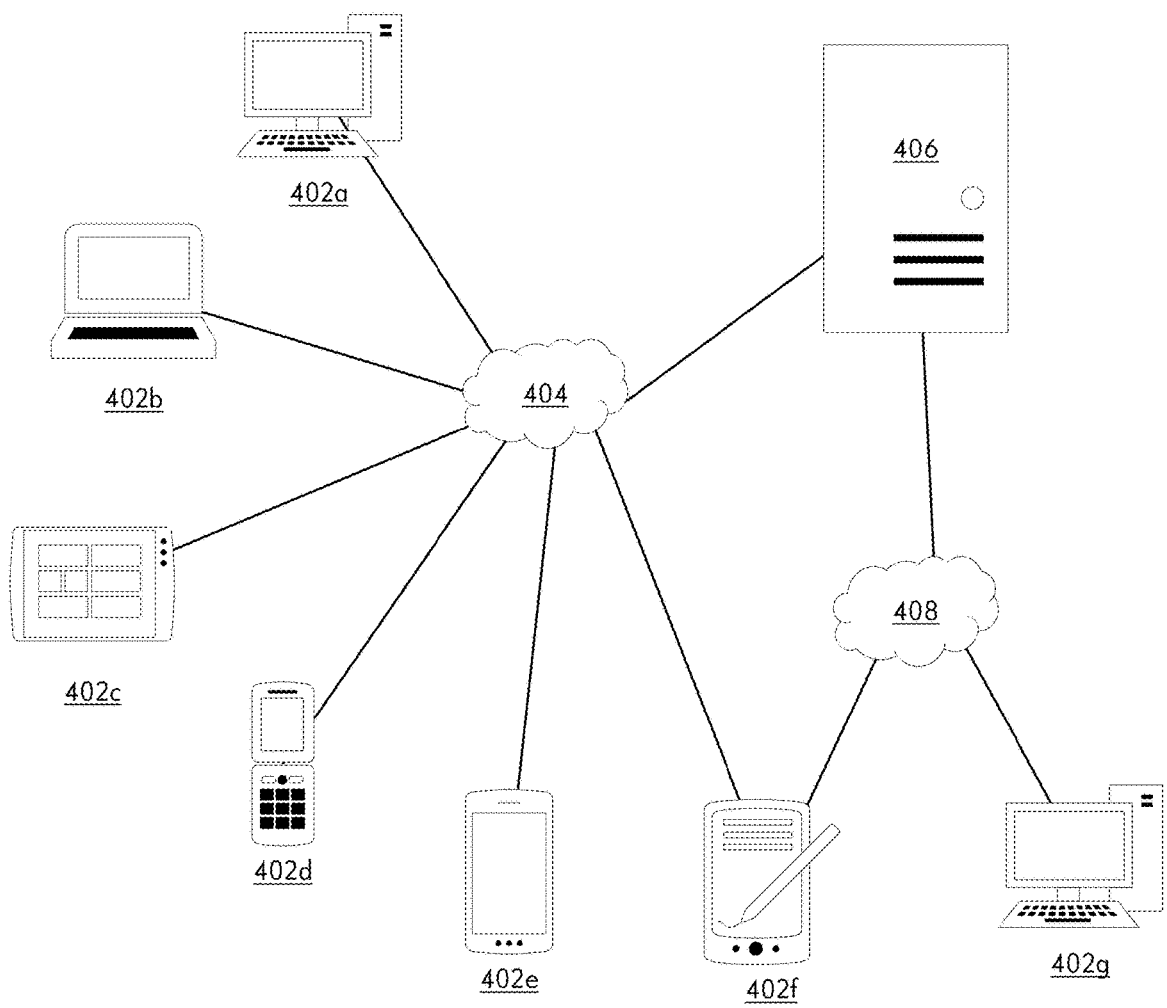

As previously noted, portions of the workflow execution system 100 may be distributed between one or more devices or components. FIG. 4 illustrates another embodiment of a workflow execution system 400 according to the disclosure. In this embodiment, the workflow execution system 400 comprises a plurality of client computing devices 402*a-g*, a network 404, and at least one server computing device 406. As shown, the client computing devices 402*a-g* may comprise desktop personal computers 402*a*, 402*g*, a laptop computer 402*b*, a slate device 402*c*, a mobile phone 402*d*, a smart phone 402*e*, and a tablet device 402*f*. Each client computing device 402*a-g* may communicate with other devices and computers via a network 404. The network 404 can be any network, such as the Internet, a wired network, a cellular network, and a wireless network. In certain embodiments, each client computing device 402*a-g* may communicate with one or more storage systems, server computing devices (e.g., the server computing device 406), cloud computing systems, or other sites, systems, or devices hosting external services to access remote data or remotely executing applications. Further, client computing devices 402*a-g* may utilize multiple networks to access the server computing device 406, such as a local connection 408. The local connection 408 may be, for example, a serial, USB, local area network (LAN), wireless, Bluetooth, or other form of local connection physically close in proximity to the server computing device 406.

In some embodiments, client computing devices 402*a-g* may be configured to execute workflows without the need to interact with other computing devices. In these embodiments, a client computing device may comprise a workflow execution engine and a backend executor, such as the workflow execution engine 112 and backend executor 114 of FIG. 1. In some embodiments, multiple backend executors may be registered to a single workflow execution engine. In these embodiments, the multiple backend executors may execute on the same hardware (e.g., a multi-processor environment), or alternately may be distributed among several components. For example, a client computing device can comprise a workflow execution engine which is configured to submit jobs for execution to one or more backend executors, which may execute on others of the client computing devices 402*a-g* or on the server 406. Similarly, in some embodiments, the server 406 can comprise a workflow execution engine, which may submit actionable jobs for execution to one or more backend executors which may be running on the client computing devices 402*a-g*. Accordingly, all or portions of the workflow execution engine 112 and its modules 302, 304, 306, 308 may be executed on the client devices 402*a-g*, the server device 406, or both. Various configurations are considered to be within the scope of the disclosure.

Figure 5:
Figure 5:
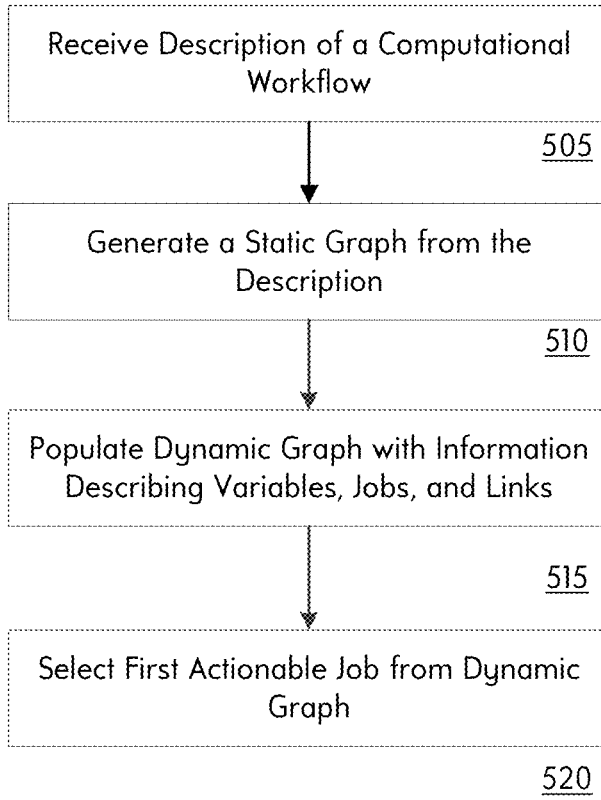

FIG. 5 depicts an exemplary method 500 of processing a computational workflow according to an embodiment of the disclosure. The method 500 can be practiced by a workflow execution engine according to the disclosure, for example. The method 500 can begin by receiving a description of a computational workflow, such as a workflow specified using the Common Workflow Language (act 505). A static graph is then generated from the description at act 510. Once the static graph has been generated, a dynamic graph is populated with a subset of information from the static graph. This can be information related to variables, jobs, and links specified by the static graph. A first actionable job (e.g., a job that is not waiting on any inputs) is then selected at act 520.

Generating a static graph from the description (act 510) can comprise identifying a minimal set of nodes from the workflow description that are required to process the workflow. A workflow description typically describes a plurality of steps. Each step can describe an action, and further have one or more inputs and one or more outputs. The steps may be ordered. For example, steps may depend from one another, in that an output for one step depends on an input from a previous step. In this regard, a workflow description can be represented as a directed acyclic graph (DAG), in which nodes represent steps and edges represent any dependencies between steps via their respective inputs and outputs. A node, or step, can be an executable, such as a command line tool. Alternately, a node can represent a container, which may contain a single tool, multiple tools, or even an entire workflow. A container node may represent another container, such as a nested workflow, for example.

In some embodiments, identifying a minimal set of nodes from the workflow description can comprise identifying, within the description, a step. If the step represents an executable component (such as a command line tool), it is added to the static graph as a node. Alternately, if the step represents a container, the step is added to the static graph as a container node. The container is then further processed to identify any steps specified by the container, which may also be added to the static graph as nodes or container nodes. Each node may further have one or more input ports and one or more output ports. Dependencies between steps are added to the graph as edges connecting certain input ports to certain output ports. Each step in the description may be processed in this manner until all of the steps specified by the description are added as nodes to the static graph.

Figure 6A:
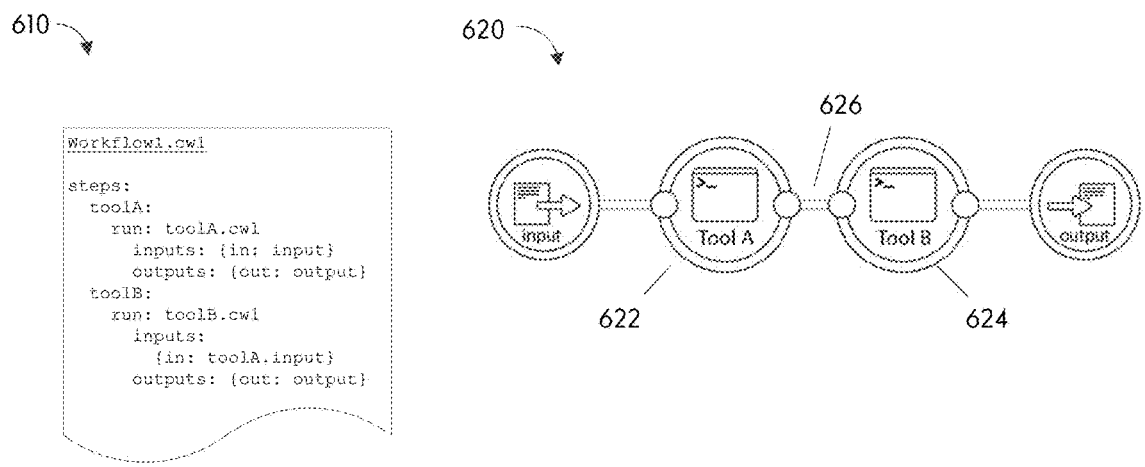
FIGS. 6A-B and 7A-B depict exemplary workflow descriptions and workflow graphs that may be processed by embodiments of the disclosure.

FIG. 6A depicts exemplary embodiments of a workflow description 610 and a corresponding static graph 620 that may be generated by, e.g. a workflow interpretation module and graph creation module according to the disclosure. As shown in FIG. 6A, the workflow description 610 includes two steps that describe executing the output generated by a tool A using a tool B. Each step of the description describes a node. Here, the nodes represent executable components. When processing the workflow description 610, the execution engine will generate a node in the static graph 620 for each step. Accordingly, the static graph 620 created by the execution engine includes a first node 622 for a first executable (Tool A) and a second node 624 for a second executable (Tool B"). Each of the nodes 622, 624 has a single input port and a single output port, indicating that each of the tools receives a single input and generates a single output. As described in the workflow description, the input port for tool B depends on the output port from tool A; in other words, an output (e.g., data file) generated by the execution of tool A should be supplied as an input for the execution of tool B. In the static graph 620, this dependency is specified as an edge 626 connecting the output port from the first node 622 to the input port of the second node 524.

Figure 6B:
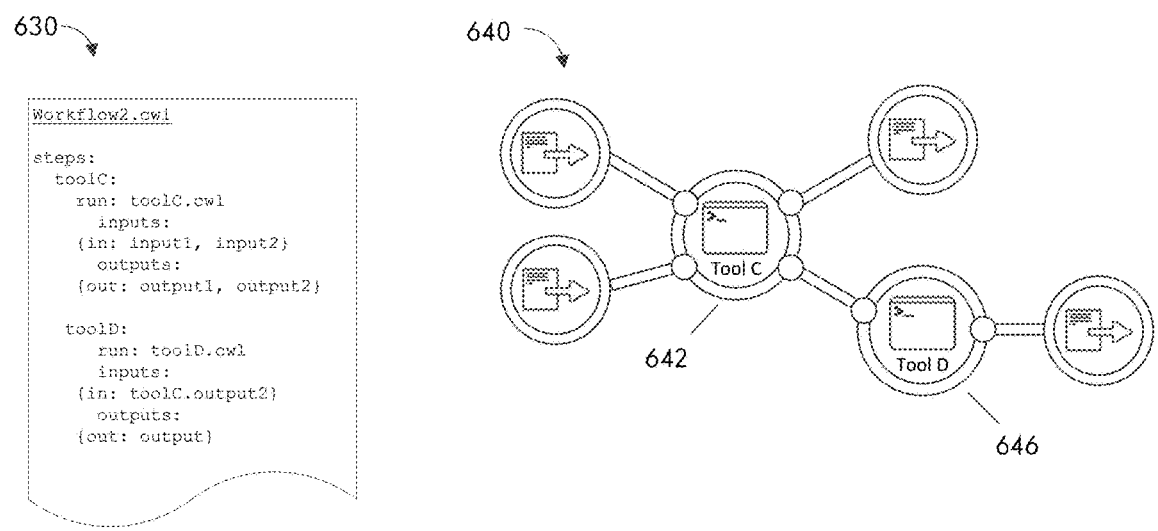

Workflow descriptions, and corresponding workflow graphs, may not always be linear structures. For example, a workflow description may include steps having multiple inputs and outputs, such that the generated graph is a multigraph with nodes that may have multiple incoming edges and/or multiple outgoing edges. For example, FIG. 6B depicts another embodiment of a workflow description 630 and a corresponding static graph 640 generated by an execution engine according to the disclosure. As shown in FIG. 6B, the workflow description 630 includes two steps that describe the execution of tools C and D. Tool C receives two inputs and generates two outputs, of which one output is supplied as input to tool D for further processing. Accordingly, the static graph 640 includes a first node 642 and a second node 644 corresponding to tools C and D. The first node 642 receives two inputs, and when tool C is executed, generates two outputs. One of these outputs is supplied to the second node 644 as an input for the execution of tool D, specified by an edge 646 connecting these ports.

Input ports and output ports do not necessarily require one to one correspondence. For example, an output port may be linked to two input ports. This is common in workflows in which a data file generated by one step is submitted to two separate steps, e.g. performing quality control and sequence alignment on a set of sequence reads simultaneously. Similarly, an input port may be linked to two output ports. This may occur in situations where the results of several tools are supplied to the same downstream tool, such as in workflows which have been explicitly parallelized by an end user.

As shown in FIGS. 6A-B, the workflow descriptions 610, 630 include steps that specify executable components, such as command line tools. However, in some embodiments, workflow descriptions may include steps that reference other workflows, and thus nodes may describe containers. For example, a workflow may include as a step a second workflow, which may be referred to as an "embedded" or "nested" workflow. As a workflow execution engine according to the disclosure encounters such container nodes in a workflow description, it adds the container as a container node to the static graph. Nodes representing workflows may be referred to as container nodes, as these nodes contain other objects, whether it be an entire workflow, or a single command line tool or executable. The graph creation module may then access that container (e.g., by reading a workflow description, or perhaps a second workflow description, via an interpretation module according to the disclosure) to identify an underlying workflow, container, or executable described within, which are then added to the static graph.

Figure 7A:
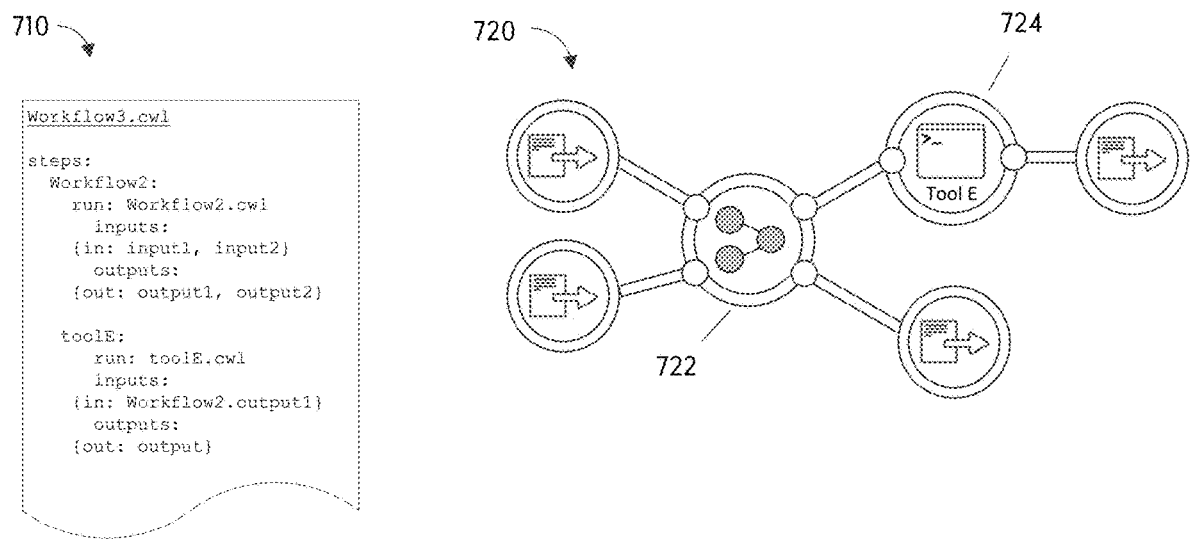

FIG. 7A illustrates an example of a workflow description 710 that includes a container. In this example, the workflow description 710 includes a step that references another workflow, here specified as a second description of a computational workflow. Initially, this step is integrated into a static graph 720 as a container node 722. In some embodiments, as container nodes are encountered, a graph creation module can evaluate those container nodes and subsequently add any steps or nodes specified by that container node to the static graph 720. This may occur after processing each of the steps in the description 710 (e.g., after generating the static graph 720 of FIG. 7A), or alternately it may occur immediately (that is, when the step is encountered, and the container node is first generated). As shown in FIG. 7A, the workflow description 710 further includes a second step representing an executable (tool E). This second step may be added to the static graph 720 as a second node 724. As described in the description 710 and incorporated into the static graph 720, the second output of the container node 722 is supplied to the input of the second node 724. Thus, on reading and processing a workflow description, a workflow graph may initially have a combination of nodes (representing executable components) and container nodes (which may represent workflows, or other wrapped components).

Figure 7B:
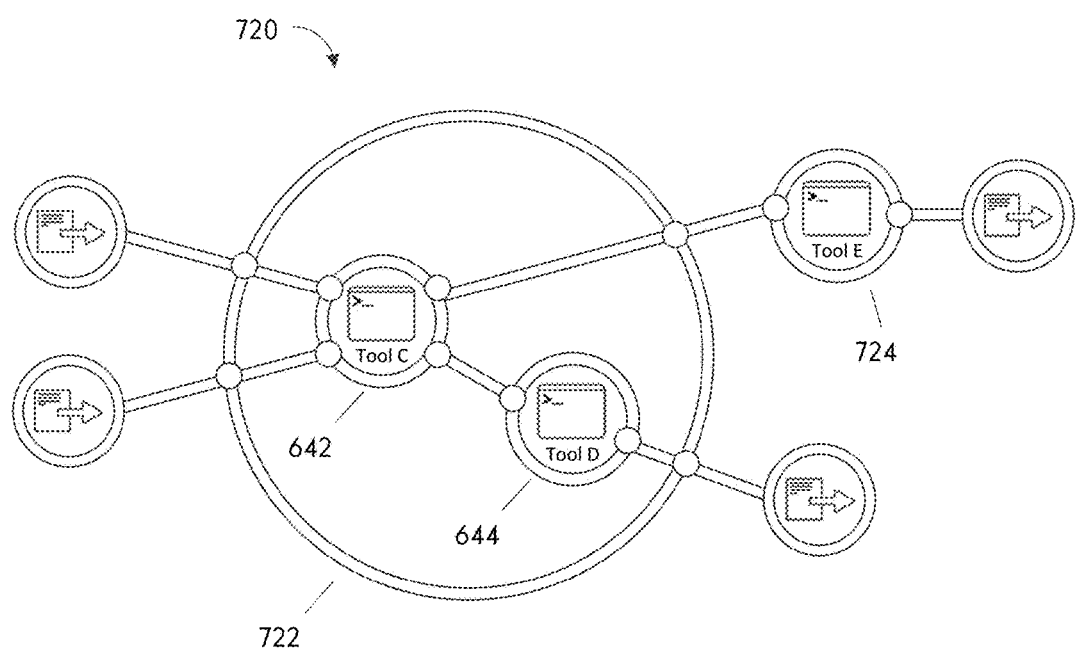

FIG. 7B illustrates how a graph creation module may modify the container node 722 with those nodes specified by the embedded workflow. As shown in the modified static graph 720 of FIG. 7B, the nodes 642, 644 are added to the graph with their specified dependencies. The workflow engine further modifies the static graph 720 such that the inputs of node 722 are linked to the inputs of node 642, the output of node 642 is linked to the first output of node 722, and the output of node 644 is linked to the second output of node 722. As shown, all of the steps within the workflow description 710 of FIG. 7A have been fully enumerated in the static graph 720 of FIG. 7B, including those specified by the embedded workflow description 630.

Enumerating all of the components of a workflow description into a static graph prior to execution is a useful feature because it can increase the efficiency of workflow processing. Whereas an embedded workflow may have multiple outputs, it can be the case that one or more downstream jobs requires only one or a fraction of these outputs to serve as their respective inputs. Conventional workflow processing engines typically wait for an embedded workflow (e.g., the embedded workflow 722 of FIG. 7A) to complete (i.e., all outputs being ready) before proceeding to the next node. Thus, valuable processing time is lost waiting for additional outputs from embedded workflows. In contrast, the static graph 720 of FIG. 7B can be processed more efficiently. As will be described in more detail below, the workflow execution engine 112 does not require an embedded workflow to complete prior to providing outputs to downstream steps because it has information regarding the entire workflow via the static graph. In the event that a workflow execution engine is executing a job within an embedded workflow (e.g., the workflow embedded within the container node 722), the engine is capable of passing values (i.e., single outputs) from the embedded workflow, once they are produced, to downstream steps immediately via any linked ports. For example, when tool C finishes execution (at node 642), its outputs may be provided immediately to both tool D and tool E, despite tool E being outside of the embedded workflow. This allows for both tool D and tool E to execute concurrently. This can lead to substantial improvements in workflow processing.

Figure 8A:
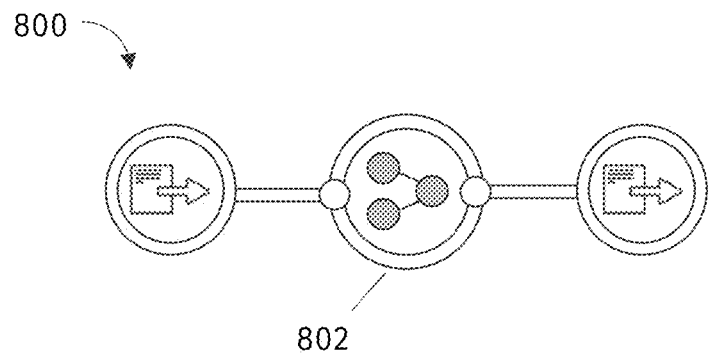
FIGS. 8A-C depict an example of a workflow graph containing multiple container nodes.
Figure 8B:
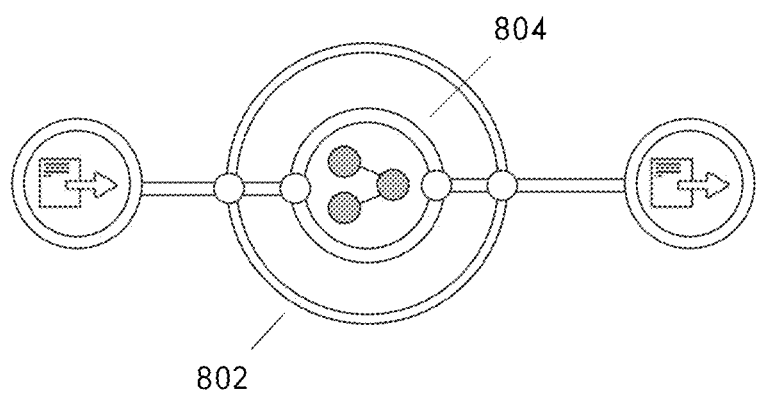
Figure 8C:
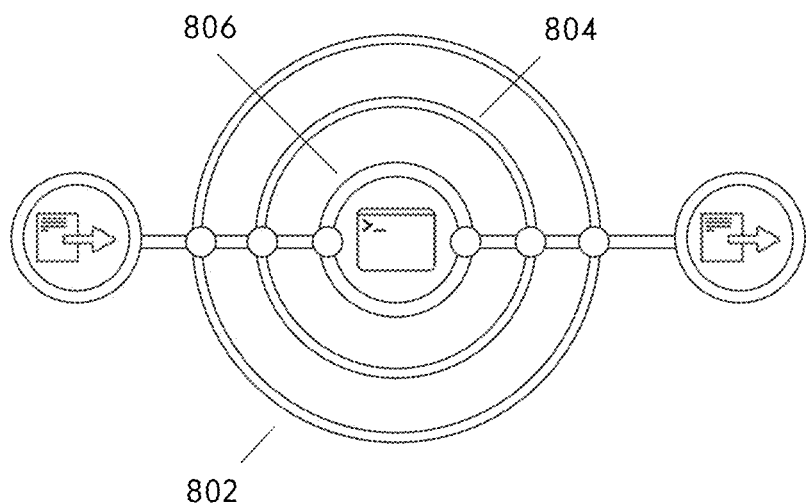

Workflows may specify multiple layers of containers. For example, as shown in FIGS. 8A-C, a workflow graph 800 generated according to an embodiment of the disclosure may store a first container node 802, which may store a second container node 804, which may finally store a node holding an executable component 806. Multiple levels of nesting may occur when using mixed protocols, e.g., a combination of CWL and WDL formats. For example, a workflow description may include a step that references a previously wrapped tool written in another format. Rather than be specified directly as an executable, it is processed as a container and added to the graph. Further, the underlying container may then specify additional nested workflows.

Once the static graph has been generated from the description (act 510), the method 500 proceeds to populate a dynamic graph with information describing a set of variables, jobs, and links (i.e., dependencies between ports) within the static graph. In contrast to the static graph, the dynamic graph can be a dynamic structure that is created on demand and modified during execution in order to optimize processing of a workflow. As previously noted, modifying the dynamic graph during execution allows for transformations and optimizations of the workflow at runtime. Further, the dynamic graph provides for the ability to inspect pending executions, allowing an execution engine to "look ahead" to identify actionable jobs that may be several hops away or positioned outside of embedded workflows.

Figure 9A:
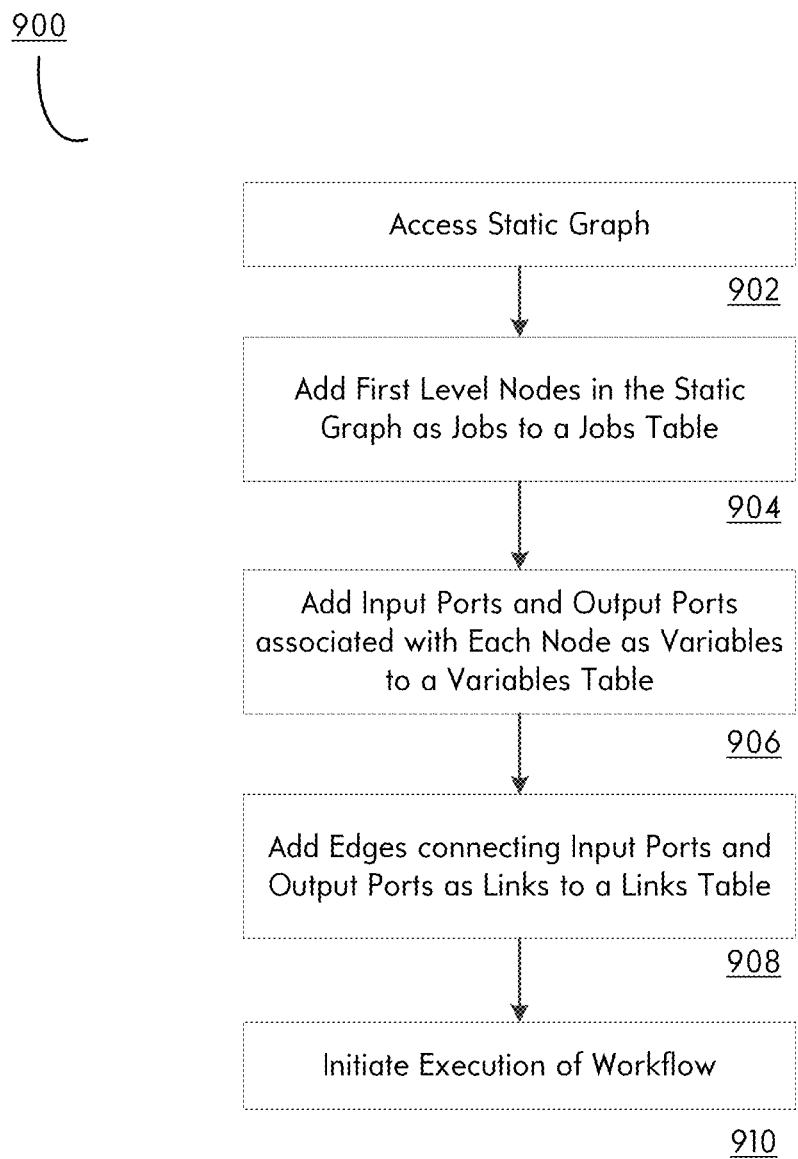
FIGS. 9A-C are flow diagrams illustrating methods of rolling out information from a workflow graph into a dynamic graph, dynamically updating the dynamic graph, and identifying actionable jobs.

FIG. 9A illustrates a method 900 of initializing a dynamic graph for processing a workflow according to an embodiment of the disclosure. In some embodiments, a static graph acts as a scaffold that an execution engine may refer to when populating a dynamic graph. The dynamic graph is then used to track the status of inputs and outputs and their associated values, identify actionable jobs, and update inputs and outputs based on their dependencies. The dynamic graph may be dynamically updated as the workflow is processed. As previously noted, adding features from a static graph to a dynamic graph may be referred to as a "rollout," and thus the method 900 can be considered to be a first rollout of the static graph into the dynamic graph.

The method 900 can begin at act 902 by accessing a static graph, such as the static graph 620 of FIG. 6A. The static graph describes a minimal set of operations required to process the workflow (e.g., all of the operations specified by a workflow description used to generate the static graph), such as a static graph generated by the method 500 of FIG. 5. The method 900 then proceeds by adding a subset of nodes in the static graph as jobs to a jobs table at act 904. The subset of nodes can be first level nodes, for example. When first performing a rollout, first level nodes can refer to those nodes in the graph that are not contained within other nodes. Initially, each node in the graph may correspond to a single job. Input ports and output ports associated with each node are then added as variables to a variables table at act 906. Initially, the values for these variables are not set. Edges in the graph, representing dependencies between input ports and output ports, are added as links to a links table at act 908. Links specify connections between ports, which may be followed to pass values for variables that have been generated by a completed job (e.g., a completed output) to downstream jobs depending from that job (e.g., a waiting input). At this stage, the initial rollout is complete and the dynamic graph may be used to initiate and orchestrate execution of the workflow at act 910.

Figures 10A, 10B, 10C, 10D:
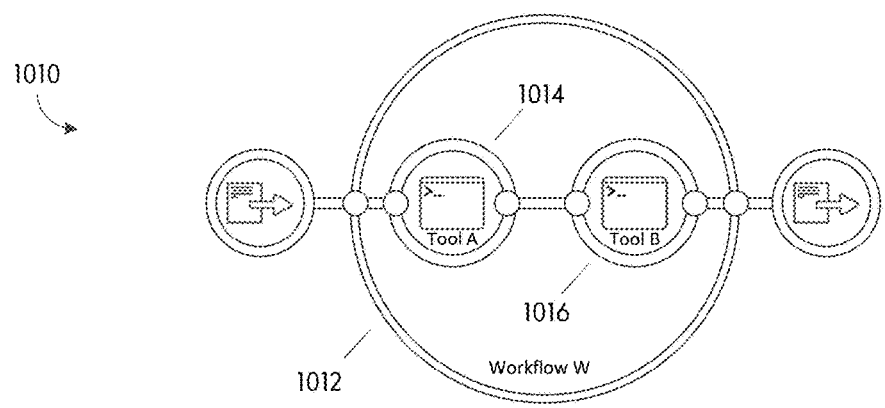

FIG. 10A illustrates a static graph 1010 and a corresponding dynamic graph 1020 that may be initialized according to an embodiment of the disclosure, such as the method 900 of FIG. 9A. As shown in FIG. 10A, the static graph 1010 comprises a container node 1012 (an embedded workflow, VV) which stores two nodes 1014, 1016 representing executable components (tools A and B). Further, as shown in FIG. 10B, in this embodiment, the dynamic graph 1020 comprises a variables table 1022, a jobs table 1024, and a links table 1026. The variables table 1022 stores information about variables, i.e., whether there are any values currently associated with any input ports and output ports of jobs in the jobs table 1024. For example, a value for a variable can be the name of a file generated by the completion of an executed job. The presence of a value for a variable indicates that that the associated port is "ready," and thus its value may be supplied to a downstream port that depends therefrom. The jobs table 1024 stores information about jobs which may be actionable. An actionable job is a job in which all of the values for its input port variables are set. Similarly, jobs can be considered "blocked" if they are waiting on values for their input port variables. Accordingly, the information about jobs can include the number of input ports on which that job is currently waiting (# In), and the number of output ports that do not yet have determined values (# Out). When # In=0, a job is no longer blocked and becomes actionable, i.e. ready. The links table 1026 stores information about which input ports are connected to which output ports; i.e., which variables are linked to other variables, such that a value generated for one variable can be supplied to a linked variable. The execution engine can efficiently process the workflow by storing, modifying, and transforming information in the dynamic graph 1020.

On an initial rollout (e.g., once a static graph has been first generated for a workflow description), the execution engine may first identify the first level nodes within the static graph 1010. As shown in FIG. 10A, the only first level node in the static graph 1010 is the container node 1012. The container node 1012 is then added as a job W to the jobs table 1024 (e.g., act 904 of the method 900 of FIG. 9). The input port and output port associated with the container node 1012 are then added as variables to the variables table (e.g., act 906). In some embodiments, any available values for these variables (e.g., the inputs supplied to the workflow itself) may not be initially set. Finally, the engine determines whether there are any edges connecting nodes that may be added as links to the links table (e.g., act 908). However, at this stage, the only first level node in the graph 1010 is the container node 1012, and so there are no links to add. As shown in FIG. 10B, the initial rollout to the dynamic graph 1020 is complete, and execution of the workflow can begin (e.g., act 910).

Figure 9B:
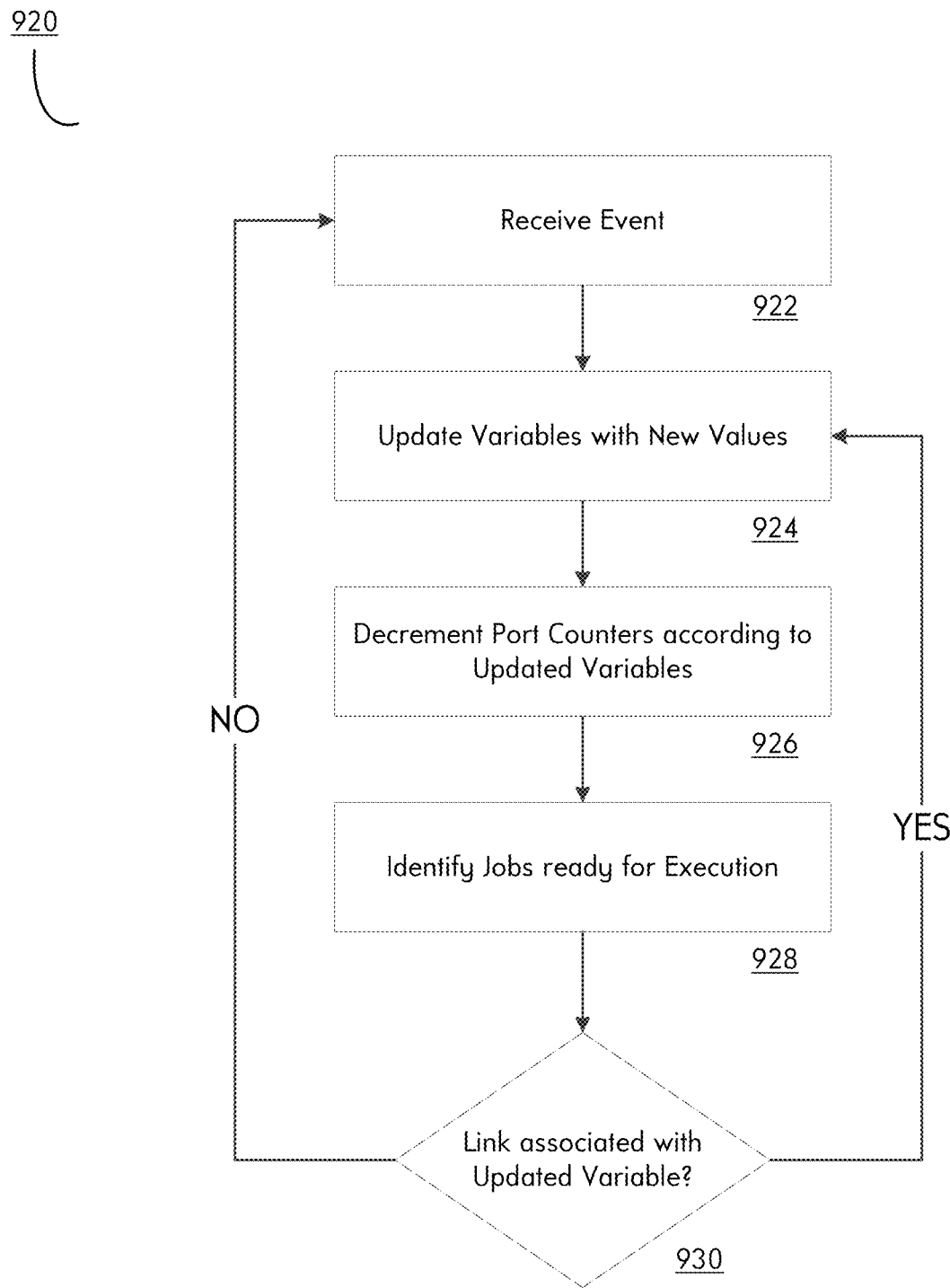

In some embodiments, workflow execution can begin by creating an initiation event, such as by providing a value for a variable to the dynamic graph 1020, which can trigger processing of the workflow. FIG. 9B illustrates a method 920 of processing a workflow according to an embodiment of the disclosure. The method 920 can be practiced by an execution engine according to the disclosure, for example. The method 920 can begin by receiving an event (act 922), such as an indication that a value for a variable is available. For example, the event can be an input update event that provides the value of an input variable for a particular job. The event can be a result of execution initialization, and can result in the provision of those input values given to the workflow within the workflow description to the variables table. Similarly, the indication may also be the result of a job completion event, in which the execution of a node has completed, resulting in the generation of data for its outputs. In either case, the receipt of the event triggers a series of actions with regards to the variables, jobs, and links stored in a corresponding dynamic graph, resulting in the updating of new values for variables by following any links, which may lead to the unlocking of previously blocked jobs.

Once the event is received (act 922), the method 920 may then proceed by updating variables with new values based on the received event (act 924). For example, the addition of a value to a variables table can result in the decrementing of at least one input port counter (# In) or output port counter (# Out) in a jobs table (act 926). If any of the jobs in the jobs table have an input port counter of zero (meaning that all of the inputs for that job are ready or available), then that job is "ready" and may be identified as a job that is ready for execution (act 928).

The method 920 may then proceed by evaluating the links table and determining whether any links are associated with the recently updated variable (decision 930). If there is a link associated with an updated variable (the YES branch at decision 930), then a linked variable is identified in the variables table and updated accordingly (act 924). In this case, the method continues to scan the variables (act 924), jobs (acts 926, 928), and links tables (decision 930) again in order to update port counters and identify jobs ready for execution. However, if there is no link associated with the updated variable (the NO branch at decision 930), then the method returns to waiting to receive an event, such as a second event indicating that another variable is ready (act 922).

As shown in the method 920 of FIG. 9B, the dynamic graph is updated in response to new events, such as job completion events. However, in other embodiments, the variables, jobs, and links tables may be continuously scanned without waiting to receive an event. Further, in some embodiments, the receipt of an event may not immediately provide a new value for a variable. For example, the event may be used simply to trigger an evaluation of the variables, jobs, and links within the dynamic graph.

As shown in FIG. 10B, the job W cannot yet begin as it is waiting on data for at least one input port (# In=1). FIG. 10C illustrates a subsequent modification of the dynamic graph 1020 in response to an indication that a variable is ready (e.g., act 922 of the method 920), which in this example comprises supplying a value associated with the input port of the static graph 1010. As shown in FIG. 10B, a value for the W.I variable is placed into the variables table (e.g., act 924). The port counter for job W is then decremented (e.g., act 926), resulting in the counter reaching a value of zero. Job W may now be identified as an actionable job for execution (e.g., act 928). No additional variables may be updated as a result of the updated variable (e.g., decision 930). Accordingly, the execution engine may now select the first actionable job from the dynamic graph for execution (e.g., act 520 of the method 500 of FIG. 5).

Figure 9C:
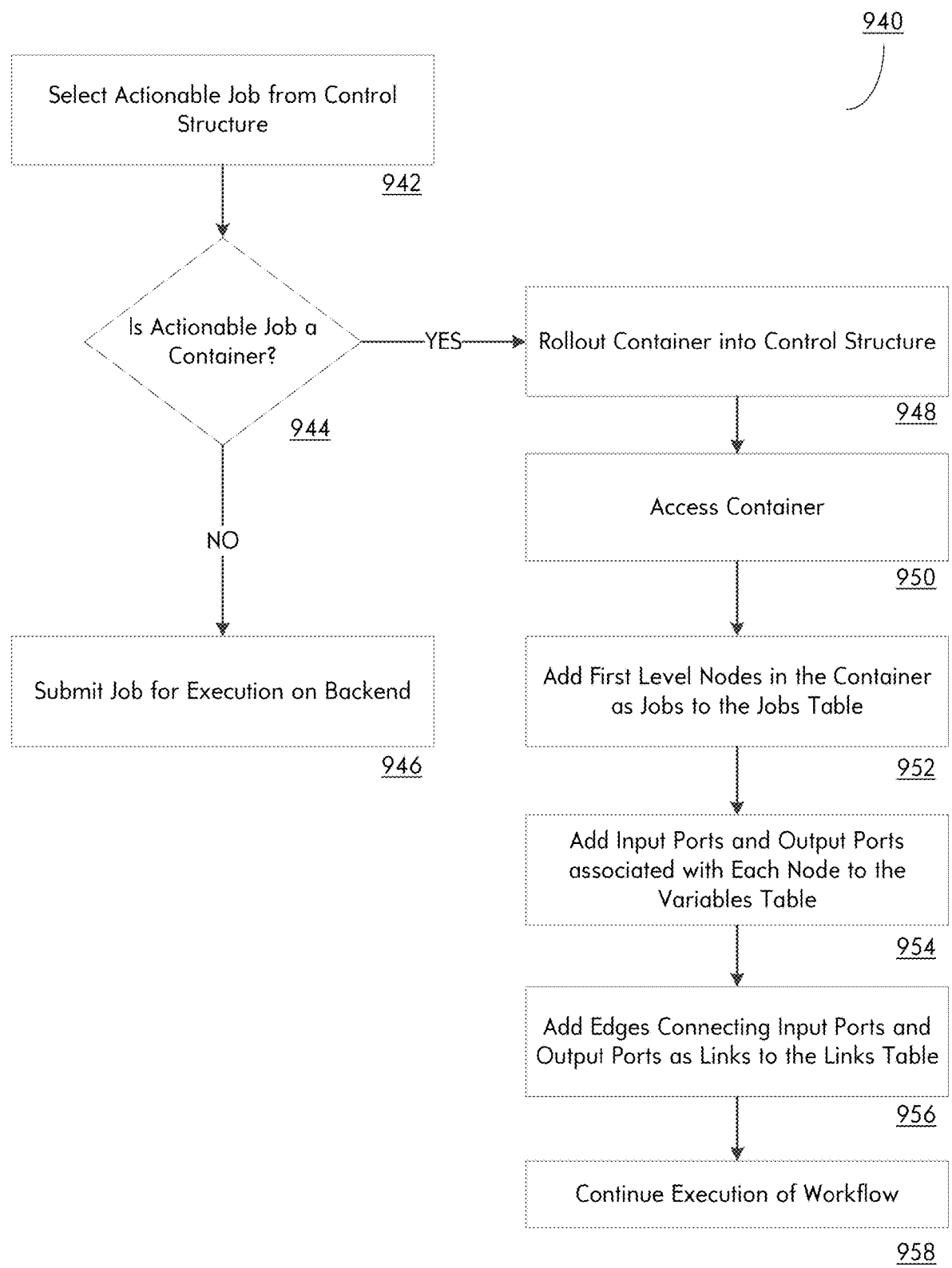

Actionable jobs within the jobs table can represent either a container node (e.g., an embedded workflow) or a node (e.g., an executable). FIG. 9C illustrates a method 940 of processing actionable jobs in a dynamic graph according to an embodiment of the disclosure. The method 940 can begin at act 942 by selecting an actionable job from a dynamic graph. It is then determined whether the actionable job represents a container (decision 944). If it is not a container (meaning that the job is an executable component), the job is submitted for execution on one or more backend executors (act 946). However, if the job is a container, a rollout of the container node into the dynamic graph is initiated (act 948).

Rolling out a container node into the dynamic graph is similar to an initial rollout (as described with respect to FIG. 9A). However, rolling out a container node into the dynamic graph differs in that it rolls out the elements of the container node, and thus the first level nodes added are those first level nodes within the container node. Accordingly, the method 940 can further comprise accessing the container (act 950), such as from a previously generated static graph. The first level nodes in the container are then added as jobs to the jobs table (act 952). Similarly, this can include the addition of nodes and container nodes into the dynamic graph, but not necessarily the contents of the newly added container nodes. Input ports and output ports associated with each node are added to the variables table (act 954). Edges connecting the first level nodes are then added as links to the links table (act 956). The rollout is now complete, and the method 940 can continue (act 958) by currying forward any variables that may be updated according to the variables table (e.g., by creating an event that triggers the scanning of variables, jobs, and links, such as by considering whether any links are associated with an updated variable according to act 930 of the method 920 of FIG. 9B), which may result in the addition of new actionable jobs.

FIGS. 10D-E illustrates the dynamic graph 1020 after a rollout of the container node 1012. Job W represents a container node, the workflow W. When the execution engine selects job W from the dynamic graph for execution, it determines that it represents a container (decision 944). The job W is then rolled out into the dynamic graph (act 948). The container is accessed (act 950), and the first level nodes 1014, 1016 are added as jobs W.A and W.B to the jobs table (act 952). The input ports and output ports of nodes 1014, 1016 are added as variables to the variables table (act 954). Additionally, the edges connecting ports between workflow W, tool A, and tool B are added to the links table as links connecting variables (act 956). The rollout of the container node 1012 into the dynamic graph 1020 is now complete.

To continue execution of the workflow, the dynamic graph 1020 may be modified (e.g., by triggering scanning of the variables, jobs, and links tables according to the method 920 of FIG. 9B) to curry the values of any updated variables and to identify actionable jobs for execution. As shown in FIG. 10E, this results in the provision of a value ("input_file") for the W.A.I variable and the decrementing of the number of waiting inputs for job W.A. Job W.A is now actionable and may be submitted for execution to a backend executor, such as the backend executor 114 of FIG. 1.

FIGS. 10E-10I illustrate subsequent modifications of the dynamic graph as the workflow is processed. Once the job W.A finishes, a job complete event is received from the backend executor, indicating that an updated variable is available to place in the variables table for variable W.A.O (FIG. 10F). The updated value for this variable is then curried according to the links table to variable W.B.I, decrementing the input counter for job W.B and unlocking job W.B for execution (FIG. 10G). Once job W.B completes, a job complete event is received, resulting in the decrementing of the number of output ports waiting for job W.B and provisioning of a variable for the output port of job W.B (FIG. 10H). Finally, the value for W.B.O is curried according to the links table to the output port W.O of the embedded workflow, decrementing the output counter for job W (FIG. 10I). At this stage, each job is complete, and thus the workflow has finished.

Figure 11:
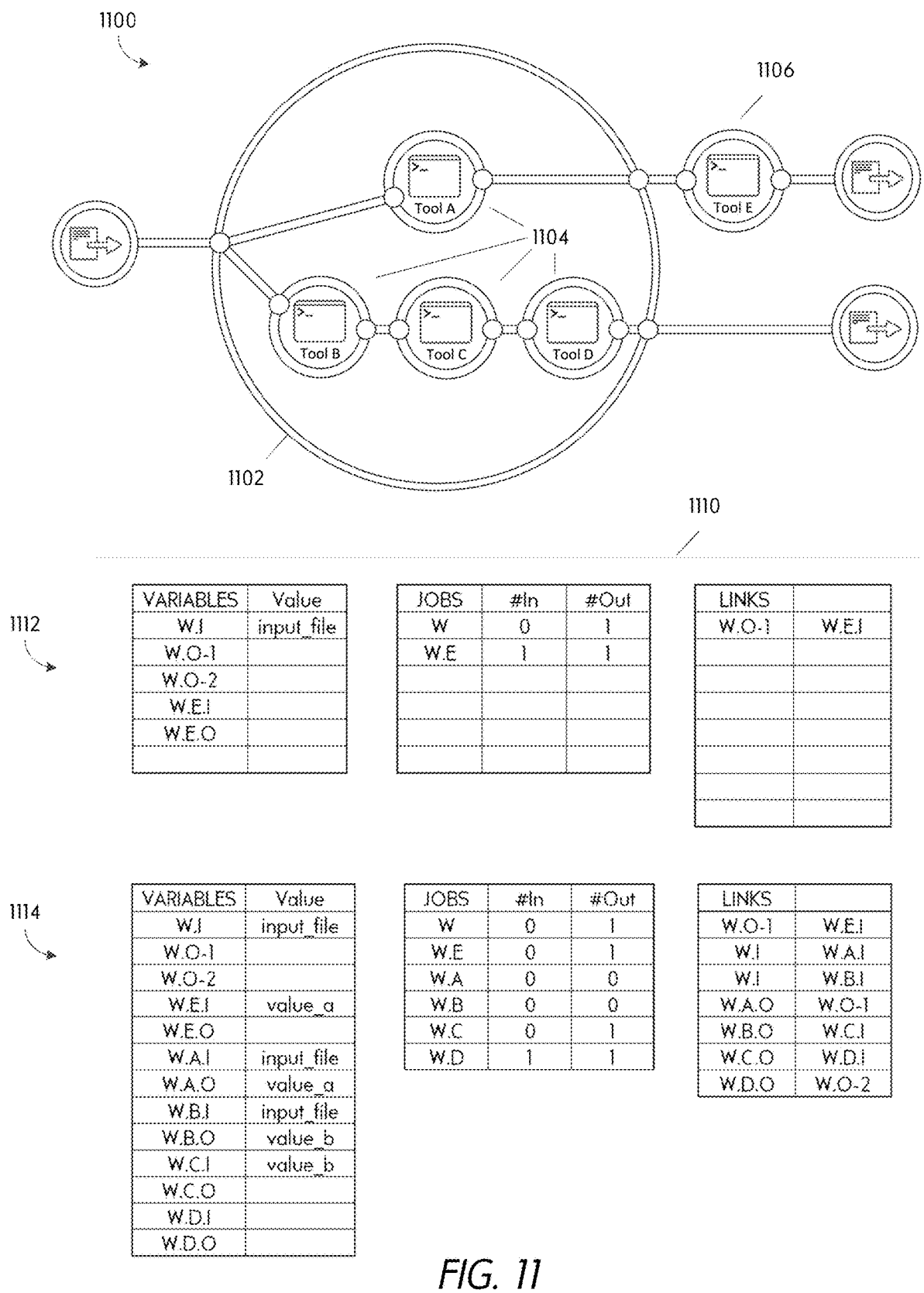

As previously noted, the ability to process container nodes from a static graph and dynamically update a dynamic graph can increase the efficiency of workflow execution. FIG. 11 depicts an example of a static graph 1100, which includes a container node 1102 representing an embedded workflow with four tools A, B, C, D (shown as nodes 1104) and a tool E outside of the embedded workflow (shown as node 1106). FIG. 11 further depicts two stages 1112, 1114 of a dynamic graph 1110 before and after the container node 1102 has been rolled out.

Consider that tool A may require 60 seconds to execute on a backend executor, whereas tools B, C, D, and E take only 30 seconds. Conventional workflow processing systems typically wait for the execution of the entire embedded workflow (i.e., the container node 1102) to complete before processing tool E. Allowing for the concurrent execution of tools A and B, this would result in a minimum execution time of 120 seconds. Workflow processing engines of the disclosure can do better. As shown in the second stage 1114 of the dynamic graph 1110, the rollout of the container node 1102 into the dynamic graph 1110, along with triggered updates of the dynamic graph (e.g., using the method 920 of FIG. 9B), results in the output from tool A to be immediately provided to tool E once it completes. Accordingly, the first output of the container node 1102 can be supplied immediately to the downstream node 1106, without waiting for the entire contents of node 1102 to complete. This ability to look ahead to downstream jobs leads to a minimum execution time of only 90 seconds for this workflow.

As previously noted, one feature of the disclosure is the ability to transform graph elements within a dynamic graph. For example, selecting a job for execution that represents a container node results in the contents of that container node being added to the dynamic graph, which allows for an execution engine to "look ahead" to find downstream jobs that may be available to run when portions of the newly added nodes complete execution. In some embodiments, other transformations may also be applied to the dynamic graph during execution to optimize processing, such as by parallelizing (which may also be termed "scattering") certain workflow steps.

Figure 12:
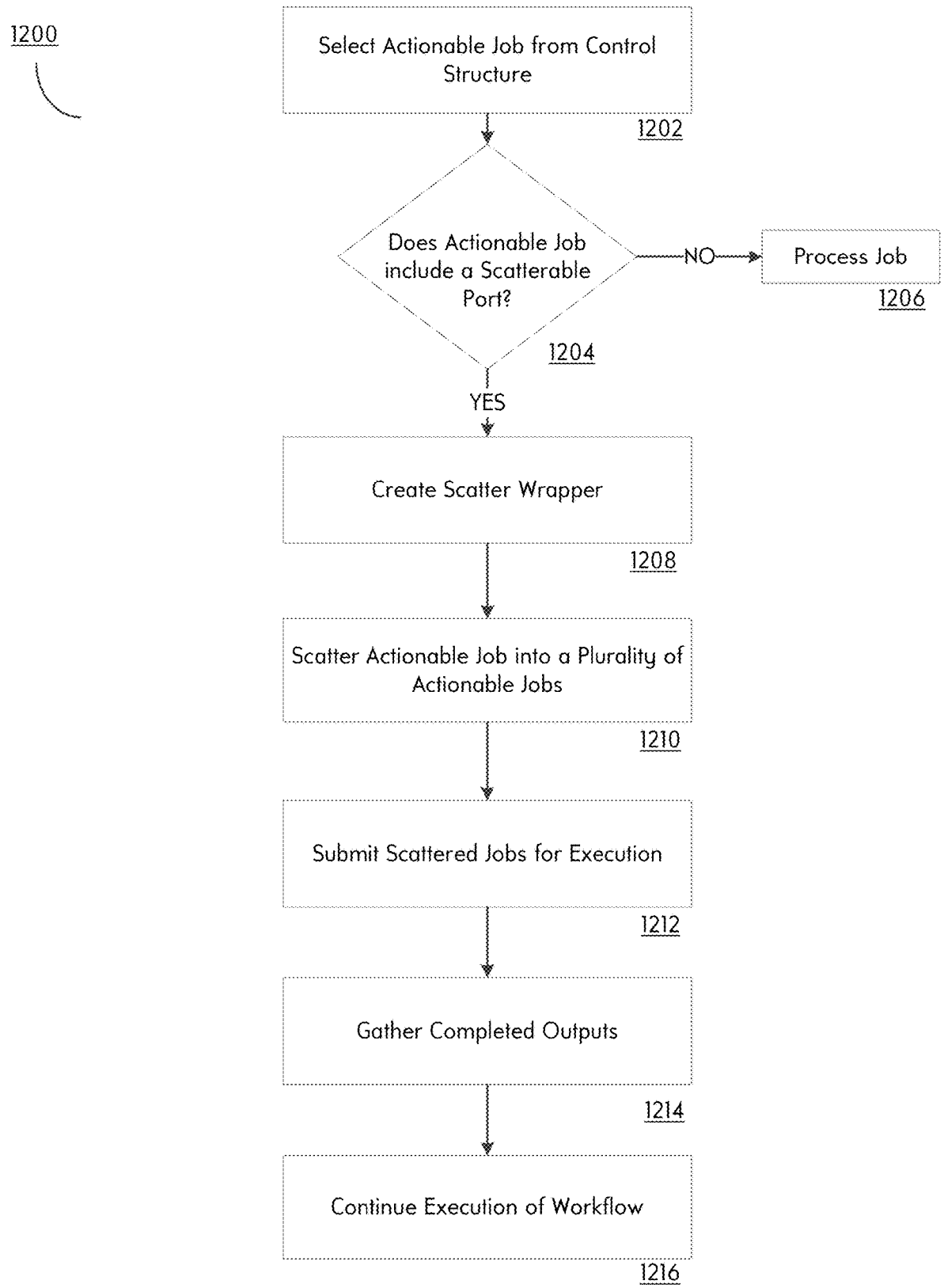

FIG. 12 depicts an exemplary method 1200 of scattering a workflow step. The method 1200 can be practiced by a workflow processing engine according to the disclosure, for example. The method 1200 can begin by selecting an actionable job from a dynamic graph (act 1202). Next, it is determined whether a port associated with the actionable job is scatterable (act 1204), i.e., whether that job may be segmented into multiple jobs and executed using multiple processors. Determining whether a port may be scatterable can be performed in a variety of ways. For example, if a port has an array of input values, one scattering strategy is to create a job for each of the elements of the array. If multiple ports have an array of values, they may be scattered according to dot products, cross products, and the like. Scatterable ports may also be explicitly specified by an end user. For example, CWL allows for a user to specify that a workflow step can be scattered using several different methods, including dot product and nested or flat cross products. See, for example, http://www.commonwl.org/draft-3/Workflow.html # WorkflowStep.

If an actionable job includes a port that is not scatterable, then the job may be evaluated and executed as previously described (e.g., by considering whether the job represents an executable or a container node). However, if a port is scatterable, the method 1200 can proceed by creating a scatter wrapper for the job (act 1208). The scatter wrapper can be a container node, for example, that is processed as a substitute for the actionable job in the dynamic graph. The scatter wrapper can also comprise additional logic that creates new jobs within the dynamic graph, such as by scattering the actionable job into a plurality of actionable jobs (act 1210). For example, if an input port is designated as scatterable and comprises an array of values, the scatter wrapper can create a job for each entry of the array, while also modifying the dynamic graph accordingly.

Once one or more scattered jobs have been added to the dynamic graph (act 1210), they may be submitted for execution (act 1212). As jobs complete, their values may be collected and combined, which may be termed "gathered" (act 1214). The gathered values may then be supplied to the next job that requires the gathered values as input.

Figure 13A:
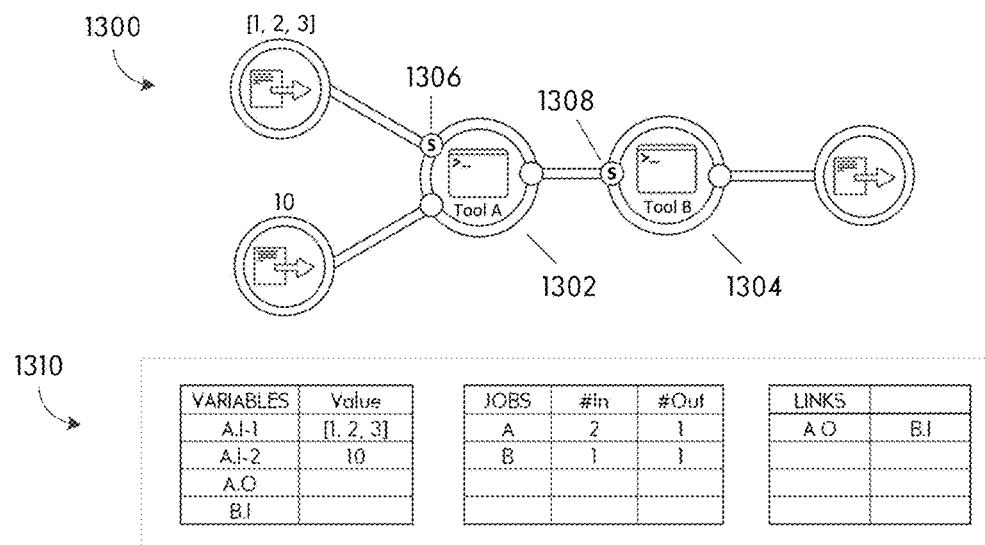
FIG. 13A depicts a static graph and a corresponding dynamic graph that includes two scatterable nodes.
Figure 13B:
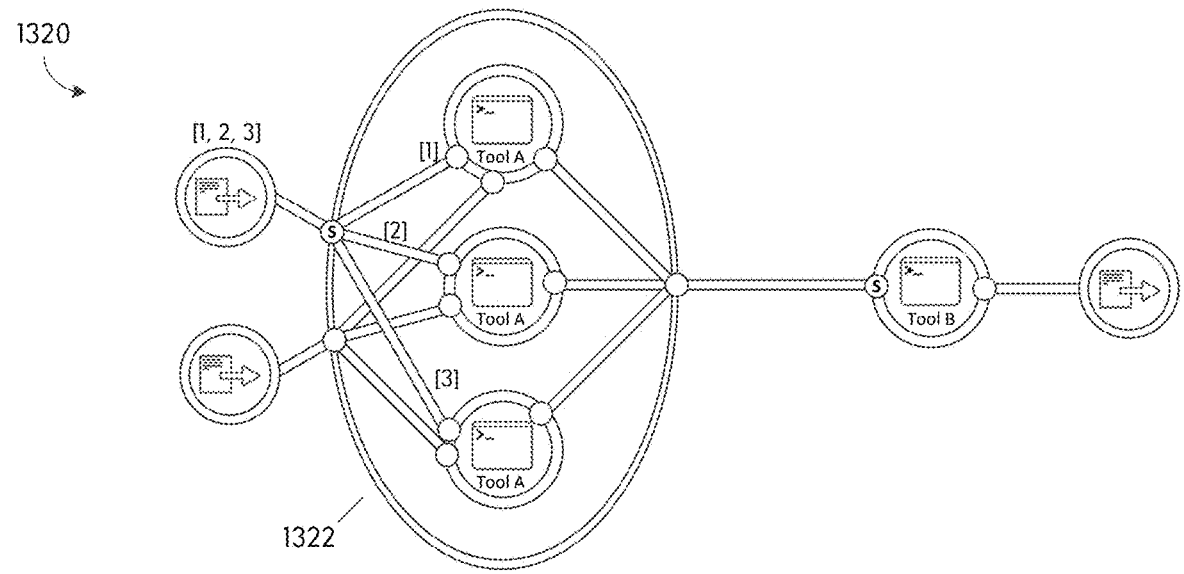
FIGS. 13B-D depict stages of the dynamic graph as the workflow is processed and the nodes are scattered.

FIGS. 13A-B illustrate an example of scattering a job, such as by the method 1200 of FIG. 12. As shown in FIG. 13A, a static graph 1300 can comprise a pair of nodes 1302, 1304 representing tools A and B, respectively. Both tools A and B include scatterable ports 1306, 1308. A corresponding dynamic graph 1310 shows that one of the inputs for the job representing tool A is an array of values. Accordingly, an execution engine may decide that this node or job can be scattered (e.g., decision 1204 of the method 1200 of FIG. 12). FIG. 13B depicts a subsequent modification to the dynamic graph 1310 in response to this decision.

As shown in FIG. 13B, the dynamic graph 1310 (additionally shown here as a graph representation 1320 of the dynamic graph) can be modified by substituting the job for tool A with a scatter wrapper 1322. The scatter wrapper 1322 is a container node in which a rollout operation (e.g., by selecting the scatter wrapper for job A for execution) can add multiple copies of the original executable node 1302, wherein each value of an array of values provided to the scatterable port may be individually provided to each copy. As shown in FIG. 13B, a rollout of the scatter wrapper 1322 generates three new jobs (represented as executable nodes) A.1, A.2, and A.3 in the dynamic graph 1310 (and as illustrated in the graph representation 1320). Further, the input values for these jobs in the variables table are each set to a single entry from the array, and the links table is updated to reflect that the outputs generated by the scattered jobs should be gathered into a single result.

Figure 13C:
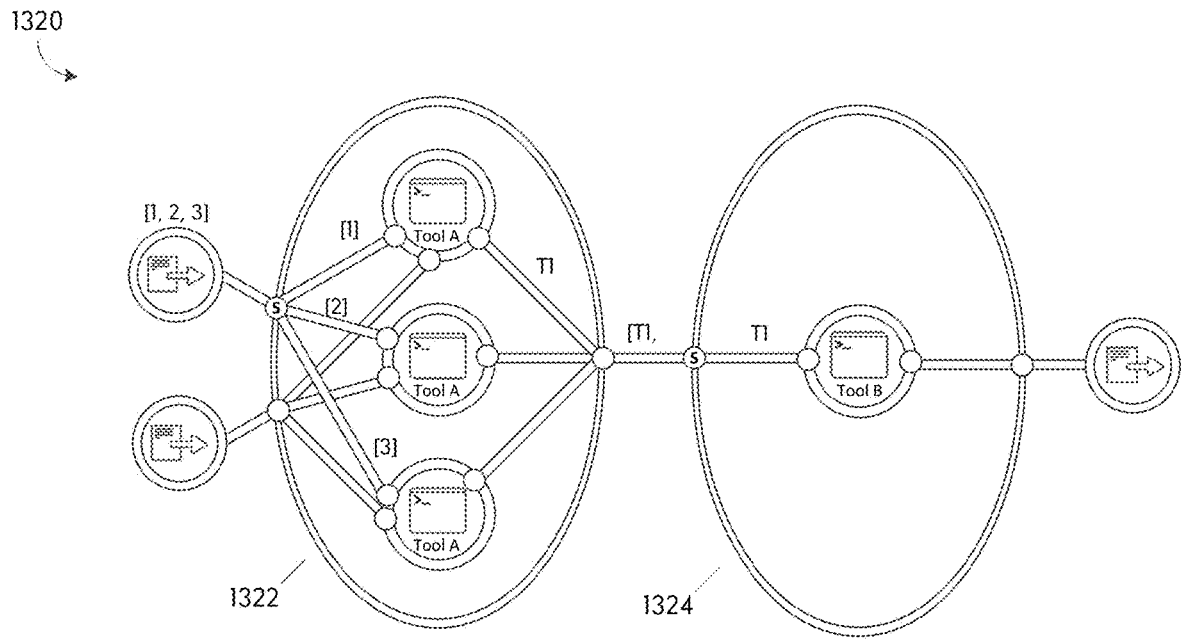
Figure 13D:
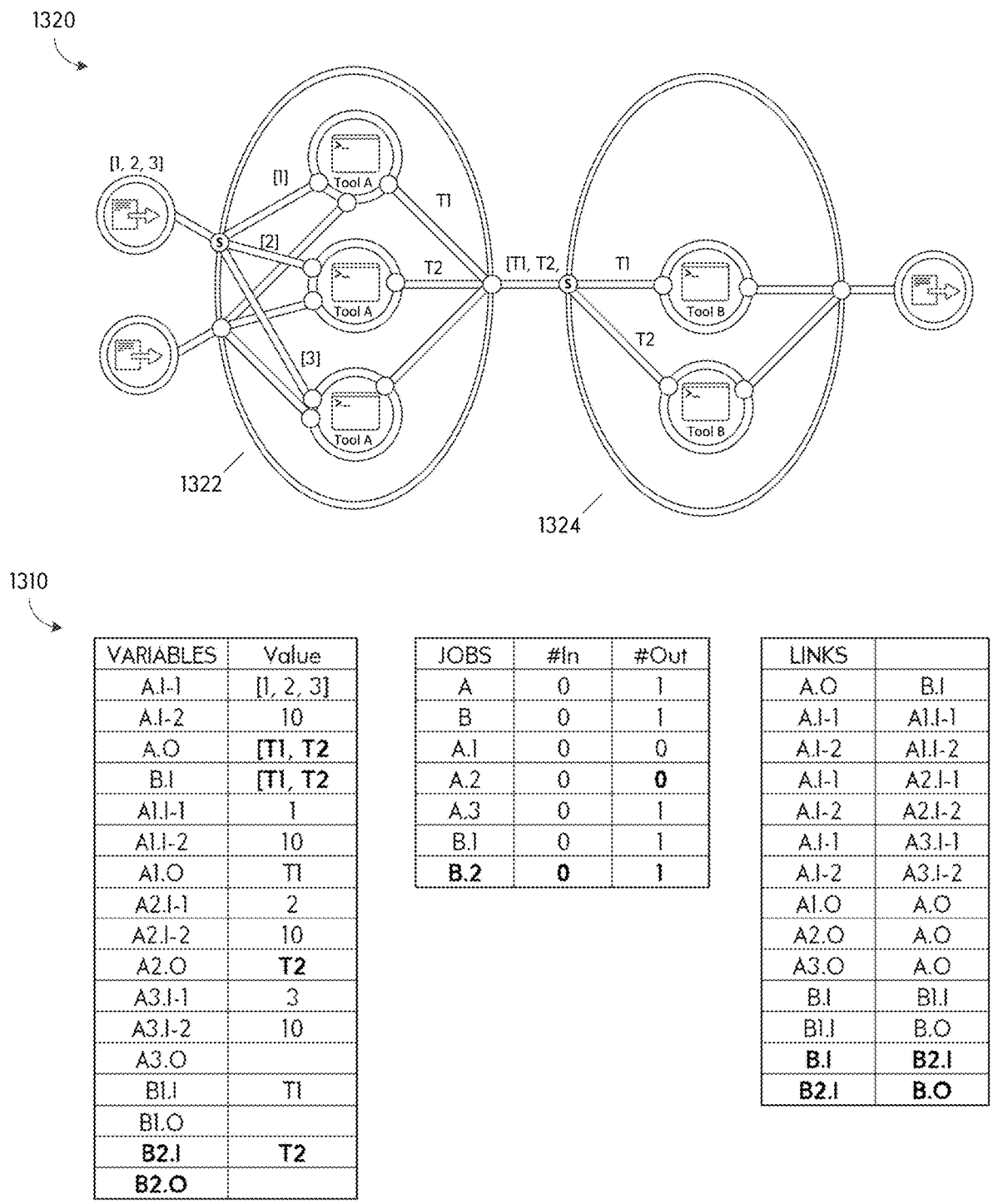

Scattering operations can extend to multiple sequential nodes. Further, scattering itself can be dynamic, in that scattered nodes and jobs can be created as output values from scattered ports become available. As shown in FIG. 13C, tool B may also have an input port marked as scatterable. When one of the scattered jobs of tool A completes, its value is updated in the dynamic graph 1310, yielding a value that may be supplied to the output port of the container node/scatter wrapper 1322. Because tool B is scatterable, the execution engine may apply a scatter wrapper 1324 to the job representing tool B. As shown in FIG. 13C, one output from tool A is available (T1, as shown for the value for the variable A1.O). Accordingly, when the value T1 is curried to the output of the scatter wrapper 1322 and then to the input of the scatter wrapper 1324, a scattered job B.1 can be created for that value, which can immediately begin processing. Similarly, as shown in FIG. 13D, when a second scattered job from tool A (job A.2) completes, a corresponding scattered job can be created (job B.2) to process that output. Thus, outputs generated from scattered jobs can be immediately processed by downstream scattered jobs, increasing efficiency and allowing for the immediate processing of scattered outputs as they are generated.

Further, in some embodiments, jobs can be grouped for execution on particular backend executors. For example, as shown in FIG. 13D, it may be more efficient for a scattered tool B to process the value T1 on the same backend executor that generated that value, removing the need to copy intermediate values (i.e., T1) to another backend executor. Similarly, all of the scattered jobs for tool A can be submitted for execution on the same backend executor, removing the need to copy tool A to three separate backend executors. Various embodiments are considered to be within the scope of the disclosure.

ADDITIONAL DEFINITIONS

All definitions, as defined and used herein, should be understood to control over dictionary definitions, and/or ordinary meanings of the defined terms.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the techniques described herein in detail, various modifications, and improvements will readily occur to those skilled in the art. Such modifications and improvements are intended to be within the spirit and scope of the disclosure. Accordingly, the foregoing description is by way of example only, and is not intended as limiting. The techniques are limited only as defined by the following claims and the equivalents thereto.

What is claimed is:

1. A method of processing a computational workflow, the method comprising:

receiving, by a workflow execution engine executing on a processor, a description of a first computational workflow, the description comprising a plurality of steps, each step having at least one input and at least one output, wherein an input from a second step depends on an output from a first step;

translating the description of the computational workflow into a static workflow graph stored in a memory, the static workflow graph not enabling transformations during runtime and comprising a plurality of nodes having input ports and output ports, wherein dependencies between inputs and outputs are specified as edges between input ports and output ports, the translating further comprising processing the description and creating a node in the static workflow graph for each step in the plurality of steps, wherein steps that specify executable tools are marked as executable nodes and steps that specify containers are marked as container nodes;

extracting, from the static workflow graph, information about a first set of nodes and placing the extracted information into a dynamic workflow graph different from the static graph and enabling transformations during runtime, the extracted information comprising jobs, variables, and links defined by the first set of nodes;

executing a first actionable job from the dynamic workflow graph, the first actionable job comprising a job for which all of its inputs are available;

receiving an indication that the first actionable job has completed, and updating the dynamic workflow graph with new information based on the indication;

determining that additional information is needed from the static workflow graph to continue processing of the computational workflow;

extracting, from the static workflow graph, information about a second set of nodes and placing the extracted information into the dynamic workflow graph;

executing a second actionable job from the dynamic workflow graph, the second actionable job comprising a job for which all of its inputs are available;

selecting a third actionable job from the dynamic workflow graph, the third actionable job comprising at least one of the container nodes;

rolling out the at least one of the container nodes so as to add information therein to the dynamic workflow graph;

executing the third actionable job; and providing an output to at least one of the nodes downstream of the second set of nodes in the computational workflow without requiring complete execution of the third actionable job.

2. The method of claim 1, wherein the static workflow graph is fully enumerated from the description of the first computational workflow prior to placing the extracted information into the dynamic workflow graph.

3. The method of claim 1, wherein the first step references a description of a second computational workflow.

4. The method of claim 3, wherein the description of the second computational workflow is written in a different format than the description of the first computational workflow.

5. The method of claim 3, wherein translating the description of the first computational workflow comprises adding the first step as a container node to the static workflow graph, accessing the description of the second computational workflow, and adding any steps described by the second computational workflow into the static workflow graph.

6. The method of claim 1, wherein translating the description of the first computational workflow further comprises adding every step specified by the description to the static workflow graph.

7. The method of claim 6, wherein the first set of nodes extracted from the static workflow graph does not include nodes corresponding to steps described by the description of the second computational workflow.

8. The method of claim 1, wherein the second actionable job comprises an executable.

9. The method of claim 1, wherein the first actionable job represents an executable described by the first step, and wherein executing the first actionable job comprises submitting the first actionable job to a backend executor.

10. The method of claim 9, wherein the backend executor is located on a device separate from the workflow execution engine.

11. The method of claim 9, further comprising:
receiving, from the backend executor, an indication that the first actionable job has completed;
updating the dynamic workflow graph with information related to an output generated by the completed first actionable job;
identifying a second actionable job from the dynamic workflow
graph; and executing the second actionable job.

12. The method of claim 11, wherein updating the dynamic workflow graph comprises:
updating a value for a variable;
decrementing a port counter for a job related to the updated value; and
determining whether any additional variables may be updated by considering
links
associated with the updated variable.

13. The method of claim 12, further comprising updating a value for a determined additional variable.

14. The method of claim 1, wherein the inputs for the first actionable job comprise an array of values, and wherein executing the first actionable job comprises placing a plurality of jobs in the dynamic workflow graph for the first actionable job, wherein each of the placed jobs comprises the executable from the first actionable job and one value of the array of values.

15. The method of claim 14, wherein the description indicates that the step associated with the first actionable job can be scattered.

16. A system for processing a bioinformatics workflow, the system comprising:
at least one computer hardware processor; and
at least one non-transitory computer-readable storage medium storing processor-executable-instructions that, when executed by the at least one computer hardware processor, cause the at least one computer hardware processor to perform:
receiving, by a workflow execution engine executing on a processor, a description of a first computational workflow, the description comprising a plurality of steps, each step having at least one input and at least one output, wherein an input from a second step depends on an output from a first step;
translating the description of the bioinformatics workflow into a static workflow graph stored in a memory, the static workflow graph not enabling transformations during runtime and comprising a plurality of nodes having input ports and output ports, wherein dependencies between inputs and outputs are specified as edges between input ports and output ports, the translating further comprising processing the description and creating a node in the static workflow graph for each step in the plurality of steps, wherein steps that specify executable tools are marked as executable nodes and steps that specify containers are marked as container nodes;
extracting, from the static workflow graph, information about a first set of nodes and placing the extracted information into a control structure different from the static graph and enabling transformations during runtime, the extracted information comprising variables, jobs, and links defined by the first set of nodes;
executing a first actionable job from the control structure, the first actionable job comprising a job for which all of its inputs are available;
receiving an indication that the first actionable job has completed, and updating variables, jobs, and links in the control structure based on the received indication;
determining that the control structure requires additional information from the static workflow graph to continue processing of the computational workflow;
extracting, from the static workflow graph, information about a second set of nodes and placing the extracted information into the control structure;
executing a second actionable job from the control structure, the second actionable job comprising a job for which all of its inputs are available;
selecting a third actionable job from the dynamic workflow graph, the third actionable job comprising at least one of the container nodes;
rolling out the at least one of the container nodes so as to add information therein to the dynamic workflow graph;
executing the third actionable job; and
providing an output to at least one of the nodes downstream of the second set of nodes in the computational workflow without requiring complete execution of the third actionable job.

17. The system of claim 16, wherein the first actionable job comprises a container.

18. The system of claim 16, wherein identifying a first actionable job from the control structure comprises finding jobs having input counters set to zero.

19. The system of claim 16, wherein the input for the actionable job depends from the output of the first actionable job.

20. The method of claim 1, wherein determining that the workflow graph requires additional information from the static workflow graph to continue processing of the computational workflow comprises executing an actionable job representing a container node.

* * * * *